United States Patent [19]
Strenkoski et al.

[11] Patent Number: 5,843,699
[45] Date of Patent: Dec. 1, 1998

[54] RAPID MICROORGANISM DETECTION METHOD

[75] Inventors: Leon F. Strenkoski, Dexter; Maureen A. Schneider, Farmington Hills; Shoba C. Swamy, Canton; Mandar S. Nagar, Yosilanti Township, all of Mich.

[73] Assignee: Difco Laboratories, Inc., Ann Arbor, Mich.

[21] Appl. No.: 826,844

[22] Filed: Apr. 8, 1997

[51] Int. Cl.⁶ .............. C12Q 1/04; C12Q 1/00; C12Q 1/18; G01N 33/53

[52] U.S. Cl. .............. 435/34; 435/4; 435/32; 435/970; 435/973; 435/308.1; 435/23; 435/24; 435/16; 536/13; 536/1.11

[58] Field of Search ............... 435/34, 4, 32, 435/970, 973, 308.1, 23, 24, 16; 536/13, 1.11

[56] References Cited

U.S. PATENT DOCUMENTS

| | | | |
|---|---|---|---|
| 4,129,483 | 12/1978 | Bochner | 195/103 |
| 4,235,964 | 11/1980 | Bochner | 435/253 |
| 4,591,554 | 5/1986 | Koumura et al. | 435/34 |
| 4,923,804 | 5/1990 | Ley et al. | 435/29 |
| 4,925,789 | 5/1990 | Edberg | 435/34 |
| 5,079,144 | 1/1992 | Carr et al. | 435/30 |
| 5,098,832 | 3/1992 | Rambach | 435/247 |
| 5,100,801 | 3/1992 | Ward, Jr. et al. | 435/286 |
| 5,145,786 | 9/1992 | Bailey et al. | 435/252.4 |
| 5,194,374 | 3/1993 | Rambach | 435/29 |
| 5,208,150 | 5/1993 | Tate et al. | 435/34 |
| 5,292,644 | 3/1994 | Berg et al. | 435/4 |
| 5,296,370 | 3/1994 | Martin et al. | 435/240 |
| 5,393,662 | 2/1995 | Roth et al. | 435/29 |
| 5,403,741 | 4/1995 | Holbrook | 435/296 |
| 5,405,773 | 4/1995 | Fung et al. | 435/25 |
| 5,411,867 | 5/1995 | Chang et al. | 435/29 |
| 5,429,933 | 7/1995 | Edberg | 435/38 |
| 5,434,056 | 7/1995 | Monget et al. | 435/34 |
| 5,443,987 | 8/1995 | DeCicco et al. | 435/29 |
| 5,447,849 | 9/1995 | Toora | 435/34 |
| 5,464,755 | 11/1995 | Bochner | 435/29 |
| 5,510,243 | 4/1996 | Boyd et al. | 435/42 |

*Primary Examiner*—Louise N. Leary
*Attorney, Agent, or Firm*—Kohn & Associates

[57] ABSTRACT

A rapid screening method for the detection and identification of target microorganisms in a sample which may contain both target microorganisms and competing non-target microorganisms includes the steps of enriching a sample in a mildly selective medium, incubating the sample in the growth medium for a predetermined amount of time, adding at least one inhibitor of the non-target microorganisms to the growth medium to discourage the growth of non-target microorganisms and to encourage the growth of target microorganisms. The method further includes the steps of incubating the sample in the growth medium including at least one inhibitor for a predetermined amount of time, performing biochemical assays specific for the identification of the target microorganisms, and detecting the presence of the target microorganisms in the sample. The invention further provides a system for the rapid detection of microorganisms in a sample.

45 Claims, 4 Drawing Sheets

RAPID MICROORGANISM DETECTION METHOD

TECHNICAL FIELD

The present invention relates to a method for detecting the presence of microorganisms in a sample. More specifically, the present invention relates to a rapid method for detecting and identifying target microorganisms in a sample which may contain other competing microorganisms.

BACKGROUND OF THE INVENTION

Foods, pharmaceuticals, cosmetics, and water are routinely tested for microbial contamination with pathogenic microorganisms. A primary technique for screening for the presence of pathogens involves a series of media (nutrient fluid) transfers starting from a non-selective enrichment media and then transferring a portion of the primary enrichment medium to a selective media. This process allows for the initiation of growth of potentially injured microorganisms in the non-selective primary enrichment media and, once the microorganisms have been revived, a small quantity of the non-selective enrichment medium is transferred into the secondary (selective) media. This process, whose duration is often defined by human work patterns and the growth patterns of the microorganisms, can take several days to complete.

For example, culturing a food sample for the presence of Salmonella typically involves the addition of approximately 20–25 grams of sample, such as meat, into approximately 225 ml of primary enrichment media. The primary enrichment media is typically non-selective, such as Buffered Peptone Water (BPW) or Universal Pre-enrichment Broth (UPB), to allow for repair of injured microorganisms. The sample is then thoroughly mixed with the primary enrichment broth and incubated for 22–28 hours at approximately 35° C.±2° C. Following this step, the sample is further selectively enriched in a growth promoting medium containing inhibitors that allow for the continued growth of a target organism, such as Salmonella, while simultaneously restricting the proliferation of most other competing microorganisms.

The most commonly used method for selective enrichment of the target organisms requires the transfer of approximately one milliliter of the primary enrichment media into two tubes containing ten milliliters of selective media such as Selenite Cystine Broth and Tetrathionate Broth (AOAC), respectively, and incubating these tubes for 22–28 hours at approximately 35° C. Other secondary enrichment media for Salmonella could include Rappaport-Vassiliadis Medium (RV) and Lauryl Tryptose Broth. This secondary enrichment step is generally followed by a detection step that can include plating the secondary enrichment broth onto solid media or by utilizing other more rapid methods, such as immunological assays or DNA probes (all media available from Difco Laboratories, Detroit, Mich.).

Many attempts have been made over the years to shorten the length of the primary enrichment step in order to reduce total assay time. Generally, it has been found that six (6) to twelve (12) hours of primary enrichment are required to obtain enough viable microorganisms for further testing. Some of these general methods are discussed below.

It has long been recognized that the potential for bacterial contamination exists in products which are designed for human consumption or use. Manufacturers and/or processors of these products destined for human consumption generally test these products to ensure the quality and safety of the products for human consumption. Such products can include raw meat, prepared food items, food preparation equipment, drinking water, bathing water, and other vectors in which microorganisms can reside which allows their contact or transfer to humans or animals.

Typically, organisms such as enteric bacteria, i.e., Enterobacteriaciae, such as Salmonella and *Escherichia. coli*, and Gram positive organisms, such as Staphylococcus and Enterococcus, are the organisms tested for in products destined for human and animal consumption or use.

These microorganisms are generally present in the colon, intestines, or fecal matter of humans or animals. When food products such as poultry, red meat, seafood, eggs, or any foods which contain these products come into contact with fecal matter during handling or processing, the potential exists for contamination and subsequent transfer of these organisms to the end users or consumers, i.e., humans.

Not only can the presence of sufficient numbers of microorganisms cause the deterioration of a food product such as by causing spoilage, additionally, if consumed by a human or animal, can also cause disease. In the United States alone, the number of cases of food poisoning associated with the consumption of contaminated food products is conservatively estimated to be in the multi-millions per year. While most human cases of bacterial food poisoning only result in acute symptomatic disease which includes nausea, vomiting, diarrhea, chills, fever, and exhaustion; for those individuals such as infants, the elderly, pregnant women, neonates, and those with immunocompromised systems, death can occur.

The total economic loss attributable to bacterial food poisoning has been estimated to reach into the hundreds of millions of dollars each year due to lost productivity, increased use of the medical insurance system, and increased use of the medical provider system.

In order to prevent the transmission of foodborne bacterial pathogens, the manufacturers and/or processors of food products routinely test samples of their products in order to identify contaminated products before the product is placed into the stream of commerce leading to human consumption. Because pathogenic microorganisms can be present in very small numbers in a food product which may contain a large number or variety of other pathogenic and/or non-pathogenic microorganisms, methods for the recovery and detection of sub-lethally injured pathogenic microorganisms have been developed. Pathogenic microorganisms are typically injured during the processing of the product destined for human consumption. That is, the pathogenic microorganisms may have undergone heating, freezing, contact with chemical additives, or mechanical processing steps which injure or debilitate the pathogenic microorganism present in the product.

A traditional method for recovering pathogenic microorganisms from a food sample involves five basic steps as set forth in U.S. Pat. No. 5,145,786 to Bailey et al. The first step is a pre-enrichment wherein the food sample is enriched in a non-selective medium to restore injured bacterial cells to a stable physiological condition. The second step involves a selective enrichment wherein selective inhibitory reagents are added to the growth promoting medium to promote the growth of selected pathogenic microorganisms while restricting the proliferation of most other bacteria. The third step involves selectively plating a sample of the enriched growth medium onto a solid selective media to physically isolate pure, discrete colonies of the suspected bacterial pathogen. The next step involves biochemical testing or screening of the pure cultures obtained from the selective plating step in order to eliminate non-target or competing organisms. The last step involves a serological analysis of the pure culture of the suspected pathogenic microorganisms in order to specifically identify the pathogenic microorganism present in the sample. The major disadvantage of this conventional method is that it is very labor intensive and time consuming. The conventional method takes on the order of three to five days to obtain a positive or negative outcome for the presence or absence of the pathogenic microorganism in the analyzed sample and is both labor and resource intensive. This lengthy analysis is often not suitable for producers of perishable products because the producer must keep the product from the consumer until the test period is over and a negative test result is obtained.

In order to eliminate the lengthy time involved with the conventional method of detection, other methods have been developed which significantly reduce the time necessary to obtain a result. The REVEAL Salmonella Test System (Neogen Corp., Lansing, Mich., U.S. Pat. No. 5,296,370) shortens the time frame necessary to obtain a negative result to approximately two days. On day one, a sample to be tested is inoculated into a non-inhibitory pre-enrichment media. After approximately two to four hours of incubation, highly selective inhibitors are added to selectively enrich for specific bacterial pathogens while inhibiting the proliferation of other microorganisms present in the sample. On day two, all of the samples are assayed by immunoassay in order to detect positive and negative samples. All positive samples are then tested further in order to confirm their identity. This method has the disadvantage that all of the samples must be analyzed by immunoassay in order to detect positive or negative cultures.

Other methods which are described and shown in Table 1, illustrate a number of commercially available test systems for the identification of Salmonella in a sample. All of the methods described in Table 1 require either the plating of selectively grown microorganisms onto a solid selective media to obtain a pure culture or require an immunological or nucleic acid based assay to be performed on every sample in order to obtain a positive or negative result for the presence or absence of Salmonella in the sample.

None of the methods described above or in Table 1 allows for a liquid enrichment of a sample to be tested for the presence of a microorganism, such as Salmonella, by adjusting the levels of Salmonella in the enrichment medium to be at or above the levels of contaminants (other microorganisms present in the sample) over a wide range of contaminant concentrations. Additionally, none of the above-described methods allow for liquid biochemical identification tests which have been fine-tuned to be reliably performed in mixed cultures. The above-described methods either require plating of an enriched culture onto a solid selective medium to obtain pure cultures prior to the performance of biochemical identification tests or require that all isolated samples be subjected to an immununoassay in order to identify the presence of a pathogenic microorganism such as Salmonella.

Therefore, it would be advantageous to have a rapid screening method for the detection and identification of target microorganisms, such as Salmonella, in a sample which may contain both target microorganisms and competing non-target microorganisms by utilizing both a liquid enrichment of a sample to be tested for the presence of a microorganism, such as Salmonella, by adjusting the levels of Salmonella in the enrichment medium to be at or above the levels of contaminants (other microorganisms present in the sample) over a wide range of contaminant concentrations and biochemical identification tests performed on potentially mixed cultures. It would further be advantageous to have a rapid method for the detection and identification of target microorganisms in a sample which may contain both target microorganisms and competing non-target microorganisms in which by utilizing biochemical tests, one would be able to rapidly screen out a large proportion of negative samples from further testing and thereby allow a manufacturer or processor of a product to release those products for consumption which have tested negative for the presence of particular pathogenic microorganisms.

The present invention not only provides a streamlined method for the identification and detection of target microorganisms in a sample, it yields the added benefits of allowing biochemical assays to be performed on potentially mixed cultures and also provides a method to rapidly screen out a large percentage of negative samples from further testing. The present invention provides a method which can be adapted for use with a number of rapidly growing Gram negative (−) organisms as well as rapidly growing Gram positive (+) microorganisms.

SUMMARY OF THE INVENTION

A method according to the present invention for the detection and identification of target microorganisms in a sample which may contain both target microorganisms and competing non-target microorganisms includes the steps of enriching a sample in a mildly selective medium, incubating the sample in the growth medium for a predetermined amount of time, adding at least one inhibitor of the non-target microorganisms to the growth medium to discourage the growth of non-target microorganisms and to encourage the growth of target microorganisms, incubating the sample in the growth medium for a predetermined amount of time, performing biochemical assays specific for the identification of the target microorganisms, and detecting the presence of the target microorganism in the sample. A system for the detection of microorganisms is also disclosed.

BRIEF DESCRIPTION OF THE DRAWINGS

Other advantages of the present invention will be readily appreciated as the same becomes better understood by reference to the following detailed description when considered in connection with the accompanying drawings wherein.

DETAILED DESCRIPTION OF THE INVENTION

Figure 1:
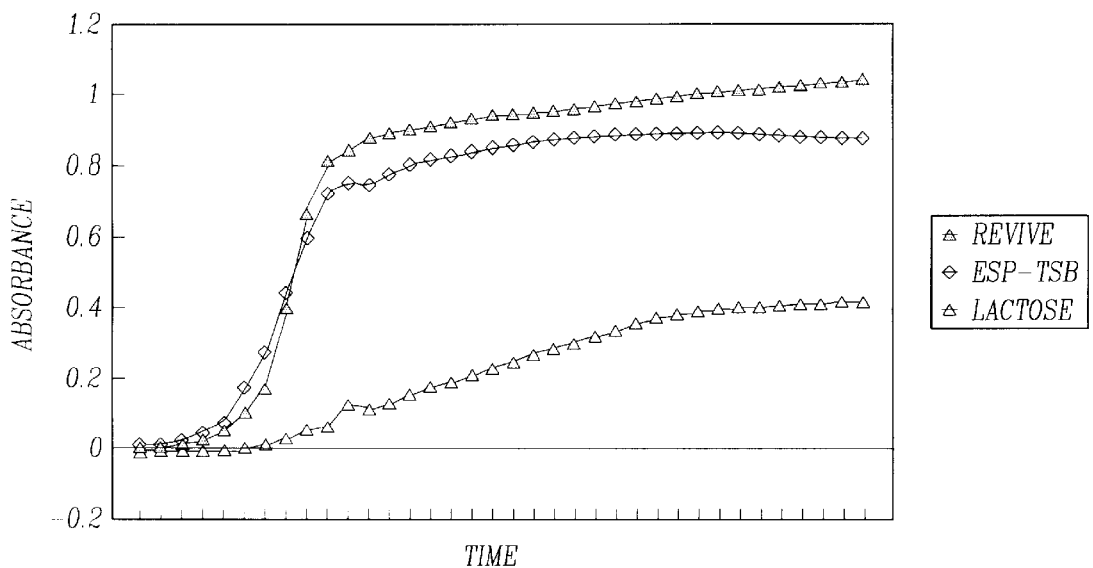
FIG. 1 is a graph illustrating the growth of heat injured *S. typhimurium* in various pre-enrichment media.

Generally, the present invention provides a rapid screening method for the detection and identification of rapidly growing target microorganisms in a sample which may contain both target microorganisms and competing non-target microorganisms. The method includes the steps of enriching a sample in a growth medium, incubating the sample in the growth medium for a predetermined amount of time, adding at least inhibitor of the non-target microorganisms to the growth medium to discourage the growth of non-target microorganisms and to encourage the growth of the target microorganisms, and incubating the sample in the medium which includes an inhibitor(s) for a predetermined amount of time. The present invention also includes the steps of performing biochemical assays specific for the identification of the target microorganisms and then detecting the presence of the target microorganisms in the sample.

Target organisms are those organisms which are being specifically tested for and/or selected for using the method of the present invention. For example, in testing a food sample, the rapidly growing target microorganisms which could be tested for could include, but are not limited to, Salmonella and/or E. coli. Since these are particular pathogens which are often found in foods, they are often "targeted" for testing in order to determine if they are present in a food sample.

In general, the rapidly growing target microorganisms have a generation time of less than one hour. Preferably, the rapidly growing target microorganisms which can be rapidly detected by the method of the present invention will have a generation time of less than thirty minutes such as Salmonella and E. coli. Generation times for these organisms can range from fifteen to forty minutes depending on the type of media in which the organisms are grown. A rich media, such as TSB, can support lower (shorter) generation times whereas a weak media, such as minimal media, can or may only be able to support higher (longer) generation times.

The target microorganisms which can be detected and identified using the method of the present invention can include any rapidly growing Gram (−) organisms such as the Enterobacteriaciae including E. coli, and rapidly growing Gram (+) organisms such as Staphylococcus aureus and Enterococcus faecalis. The target microorganism can be detected and identified by tailoring the specific inhibitors and biochemical reagents to the target organism(s) to allow for the use of these inhibitors and biochemical tests in mixed culture as discussed below in greater detail.

In order to screen a sample for the presence of the target microorganism in the sample, a suitable sample i.e., a food sample, pharmaceutical sample, or other, is obtained. A sample of suitable size and weight is placed in a suitable container containing a suitable pre-enrichment media.

In a preferred embodiment of the present invention, the container is constructed in the form of a bag. The bag can be constructed of any suitable resilient plastic material such as polyester/polyethylene laminate. Because of the nature of the samples which may be tested, such as a food sample, the container should be constructed of a resilient material so that it can withstand homogenizing or "stomaching" of the sample disposed within the bag in order to expose the microorganisms located within the sample. The container can also be made of any other suitable material known to those skilled in the art.

The container can also include a closure such as a "zip-lock" type closure to prevent spillage of the contents of the container and, further, to prevent contamination of the contents of the container. The container can also include a filter which allows fluid to pass therethrough while preventing particular matter, such as food particles, from passing therethrough.

Following dispensing of the sample in the container of pre-enrichment media, the sample, can be stomached or homogenized within the bag utilizing means well known to those skilled in the art. (Stomacher Lab-Blender, Seward Medical, London, U.K.). The sample is stomached within the bag containing the pre-enrichment media for a period of approximately thirty seconds to five minutes. The container is then incubated at a temperature suitable for growth of the target microorganism. For example, if the target organism is Salmonella, then the container could be incubated at approximately 35° C.±2° C. The incubation in the pre-enrichment media (pre-enrichment step) is carried out to resuscitate sub-lethally injured microorganisms that are present in the sample.

The pre-enrichment step may be carried out for a period of approximately two to six hours in duration. Preferably, the pre-enrichment step is carried out for period of approximately four hours in duration.

The pre-enrichment media can include any general, non-selective and/or mildly selective growth medium known to those skilled in the art. This can include media such as REVIVE ((Neogen Corp., Lansing, Mich.) TSB media (Difco, Detroit, Mich.) or other similar type media. The pre-enrichment medium can be any non-selective liquid media to a mildly selective growth medium allowing for the rapid recovery and growth of potentially injured target organisms and which will allow sufficient bacterial growth to allow for sufficient growth of the target organisms in such a way that the pre-enrichment medium will contain at least one viable target organism if such organism existed in the original sample. Examples of suitable non-selective growth media (which are available from Difco Laboratories, Detroit, Mich.) include Tryptic Soy Broth (TSB), Buffered Peptone Water (BPW), Universal Pre-enrichment Broth (UPB), Listeria Enrichment Broth (LEB), and other non-selective or mildly selective media known to those skilled in the art. The preferred pre-enrichment media for use in the present invention is the modified-TSB media.

In the present invention, the pre-enrichment media can also include the addition of a selective inhibitor or mildly selective inhibitor such as an antibiotic. In the method of the present invention, the antibiotic novobiocin can be added to the modified-TSB media prior to the addition and incubation of the sample in order to provide a selection pressure in favor of the growth of Salmonella. The novobiocin or sodium salt thereof can be added in a concentration of between 1–50 $\mu$g/ml. Preferably, the concentration of the novobiocin is approximately 20–40 $\mu$g/ml with the preferred concentration being approximately 25 $\mu$g/ml of pre-enrichment media. Alternatively, other antibiotics such as vancomycin, penicillin, ampicillin, and amikacin can be utilized in appropriate concentrations. Other target organism selection enhancing additives known to those skilled in the art can be added to the pre-enrichment broth to favor the growth of the selected target microorganism over other competing non-target microorganisms present in the sample.

Following the pre-enrichment step or resuscitation of the injured target microorganisms in the sample, a selective enrichment step is carried out to further inhibit competing non-target microorganisms which have not been inhibited during the pre-enrichment step. For example, when Salmonella is the target microorganism, the selective enrichment step is carried out to further inhibit other Gram (−) bacteria thereby promoting or encouraging the growth of Salmonella in the mixed culture.

At least one selective inhibitor or mixtures thereof can be added at the end of the approximately four hour incubation of the pre-enrichment step. Approximately ten milliliters of the inhibitor mixture is added to the container containing the pre-enrichment media and the sample. This time point is critical since the growth levels of the competing non-target microorganisms will increase to levels that would interfere with obtaining positive reactions to the biochemical analysis unless the growth levels of the competing non-target microorganisms are inhibited. The container with the selective inhibitors is further incubated for an additional approximately six to eight hours (when utilizing semi-automated transfer) or for sixteen to twenty hours (when utilizing manual transfer) at a temperature range of approximately 33° C. to 43° C. depending on the target microorganism as discussed above. This incubation time window is critical as during this time window, the organisms can be transferred at any time as the ratio of target organisms to non-target microorganisms is suitable for biochemical assaying. Preferably, the container with the selective inhibitor(s) is further incubated for an additional approximately eight hours at approximately 35° C.±2° C.

The selective inhibitor(s) or mixture thereof can include compounds or reagents which are known to inhibit the growth of non-target microorganisms while encouraging the proliferation or growth of the target microorganisms. For example, if the target microorganism is Salmonella, it has been found that a mixture of magnesium chloride, malachite green, and crystal violet can be added to the pre-enrichment media present in the container to yield excellent inhibition of non-target microorganisms. The concentration of the malachite green in the solution ranges from approximately 10 mg/l to 50 mg/l (0.003%–0.03 w/v), the magnesium chloride concentration ranges from approximately 0.5 g/l to approximately 2 g/l (0.1%–1.0% w/v), and the concentration of the crystal violet ranges from approximately 0.001 g/l to 0.010 g/l (0.0005%–0.001% w/v). The preferred concentration of the inhibitor mixture for Salmonella includes 30 mg/l malachite green, 0.005 g/l crystal violet, and approximately 1.0 g/l magnesium chloride. Other inhibitors can include bile salts, sodium deoxycholate, sodium selenite, sodium thiosulfate, sodium tetrathionate, sodium sulphacetamide, mandelic acid, selenitecysteine tetrathionate, sulphamethazine, brilliant green, malachite green, crystal violet, tergitol 4, sulphadiazine, amikacin, and novobiocin.

After incubation of the sample in the presence of the inhibitor(s) of the non-target microorganisms, an enhanced enrichment step is carried out to eliminate a large proportion, approximately 70–90% or more of the samples which are found to be negative for the presence of the target microorganism. At the end of the approximately twelve hour incubation, (four hours pre-enrichment+eight hours selective enrichment for semi-automated transfer) or at the end of the approximately twenty hour incubation, (four hours pre-enrichment+sixteen hours selective enrichment for manual transfer) an aliquot of the sample can be transferred from the original container into separate media receiving vessels wherein specific biochemical assays determinative of the presence of the target microorganism are undertaken. The transfer of the aliquot of the sample can be accomplished either by manually transferring a predetermined amount of the sample into the media receiving vessel or can be accomplished by automated means such as that described in a presently pending application U.S. Ser. No. 08/503,081 to Eden et al., filed Jul. 14, 1995, and assigned to the assignee of the present invention.

Alternatively, the sample can be allowed to incubate overnight (approximately sixteen hours) and then can be either manually or semi-automatically transferred from the original container into separate media receiving vessels wherein specific biochemical assays determinative of the presence of the target microorganism are undertaken. The transfer of the aliquot of the sample can be accomplished either by manually transferring a predetermined amount of the sample into the media receiving vessel or can be accomplished by automated means such as that described above.

Thus, the present invention provides a system in the form of a manual, semiautomatic or automatic system for rapidly detecting a target microorganism in a sample which may contain both target microorganisms and non-target microorganisms. The system can be generally defined as including a container for containing a sample therein, growth inhibitors for inhibiting the growth of non-target microorganisms, biochemical reagents for identifying the target microorganisms, and detecting assays for identifying the target microorganisms.

The biochemical tests or reagents specific for identification of the target microorganisms can include antibiotics, dyes, and other biochemical reagents indicative of particular microorganisms such as by targeting sugar fermentation, decarboxylation, cleavage by unique enzymes, and/or use of unique combinations of dyes (including fluorescent dyes). Additionally, other reagents used in the detection and identification of microorganisms known to those skilled in the art may be practiced with the present invention. For example, for the detection of Salmonella, the aliquot of the sample from the container can be transferred into a media receiving vessel, such as a test tube, which can contain reagents necessary for performing a MUCAP (methylumbelliferyl caprylate) test. Additional tubes may be utilized which contain reagents for farther biochemical tests such as $H_2S$ tests, media specifically designed to indicate the presence of lysine decarboxylase, ornithine decarboxylase, or arginine decarboxylase in a suitable base media such as LICNR (lysine-iron-cystine-neurtal red broth, Difco Manual) base media, fermentation reaction media such as for dulcitol, propylene glycol (PG), glucuronic acid (GA), in a peptone base, and a citrate utilization can also be assayed using Simmon's citrate agar (Difco Manual) or citrate medium (magnesium sulfate, ammonium dihydrogen phosphate, sodium citrate, yeast extract, sodium chloride) placed in the media receiving vessels.

The preferred biochemical reagents or tests for Salmonella include a tube which includes an $H_2S$ strip in the MUCAP test and one tube with reagents indicating lysine decarboxylation.

Following the addition of the aliquot of the post-incubation sample into the separate media receiving vessels or tubes containing the biochemical reagents, the samples are incubated for approximately twelve–fourteen hours with twelve hours being the preferred incubation time (a complete enrichment of twenty-four hours).

The results of the biochemical assays, specific for the target microorganisms, allow for the immediate elimination of those samples which are found to be negative for the presence of the target microorganisms. That is, since the biochemical assays or tests have been specifically designated to indicate the presence of the target organism in a mixed culture including target organism and non-target organisms, a negative reaction to these specific biochemical assays indicates the absence of the target microorganisms in the sample and, therefore, allows for the immediate elimination of the sample from consideration.

The detection of a positive or negative test can be done visually, by fluorescence, gas production, and/or by any other suitable detection means known to those skilled in the art.

Following a positive outcome or result after the specific biochemical assays, further microbiological analyses such as immunoassay, DNA probing, serological analysis, plating on selective media, or the like can be undertaken in order to positively identify those samples which are positive for the target microorganism.

By utilizing the method of the present invention, a sample tested which may have contained an initial inoculum of 1 cell/225 ml of target microorganisms, can be enriched to $10^0$–$10^1$ cfu/ml after pre-enrichment, $10^3$–$10^4$ cfu/ml following selective enrichment, and greater than $10^6$ cfu/ml following enhanced enrichment. At these final concentrations, biochemical assays performed in mixed cultures can be adequately performed to test for the presence of the target microorganisms.

The present invention also includes a kit containing the pre-enrichment media, selective inhibitors, and specific biochemical assay reagents necessary for performing the rapid screening method for the detection and identification of target microorganisms, all of which are described above.

EXAMPLES

Heat Injury Methodology

Materials

Tryptic Soy Broth (Difco Lot #800543)
Tryptic Soy Agar (Difco Lot #66932JA)
NaCl (Sigma Chemicals 109F/0498)
Bacto-Peptone (Difco Lot #37680JA)
TSA+2% NaCl
TSA
0.1% Peptone dilution blanks (9.0 ml per tube)
Water bath (Blue M)

Procedure

The water bath (with an agitator) was set at 55° C. and was filled to almost full and turned on to warm up for thirty to forty-five minutes with its lid on. Sterile 100 ml capped media bottles each containing 18 ml of TSB were placed into the water bath in a rack for approximately fifteen-twenty minutes prior to the start of the heating assay.

Enumeration of Cultures Prior to Heating Assay ($T_o$)

1.) S. enteritidis and S. typhimurium were grown in TSB for eighteen to twenty-four hours at 35°±2° C.

2.) Serial dilutions to $10^{-6}$ were performed the day of the assay in sterile peptone dilutions blanks.

3.) A 100 μl suspension from $10^{-6}$ dilution was spread plated onto the TSA plates. The plates were dried in a biohood for fifteen to twenty minutes and incubated at 35°±2° C. overnight.

Heat Injury Assay

1.) 2 ml each of S. enteritidis and S. typhimurium were added to the pre-heated TSB broth in two separate media bottles (1:10 dilution) and were placed in the heated water bath for fifteen minutes.

2.) After fifteen minutes, the media bottles with the inoculum were quickly cooled in an ice bath to stop further injury.

3.) 1 ml aliquots were removed from the media bottles and transferred aseptically to a 9 ml peptone/saline dilution blank ($10^{-2}$).

4.) Serial dilutions up to $10^{-5}$ were performed.

5.) A 100 μl suspension from −2 and −3 dilutions were spread plated onto the TSA and TSA plus 2% NaCl plates. The plates were dried for fifteen-twenty minutes in the biohood and then incubated at 35°±2° C. overnight.

The formulas used for calculating heat injury were as follows:

$$\% \text{ Heat Injury} = 100 \times \frac{\text{cfu/ml on } TSA \text{ after 15 minutes} - \text{cfu/ml on } TSA + 2\% \text{ NaCl after 15 minutes}}{\text{cfu/ml on } TSA \text{ after 15 minutes}}$$

$$\% \text{ Heat Kill} = \frac{\text{cfu/ml on } TSA @ T_0 - \text{cfu/ml on } TSA @ T_{15}}{\text{cfu/ml on } TSA @ T_0} \times 100$$

Results

Utilizing the method set forth above for heat injuring bacterial cells to simulate target cells which are sub-lethally injured during testing of a sample, it was found that the injury times in a 55° C. water bath necessary to create a 92–98% injury population ranged from fifteen to thirty minutes.

Growth Medium Selection

In order to ascertain a suitable growth medium for the resuscitation and growth of microorganisms in a sample, modified-TSB and REVIVE media were compared for their performance with S. typhimurium. The six hour plate count before transfer of the inocula to a Biotek light absorbance reader (Bio-Tek Instruments, Winooski, Vt.) is shown in Table 3. A 4.1 cfu/ml inocula of heat injured S. typhimurium was inoculated into modified-TSB, REVIVE, and lactose broth at approximately 35° C.±2° C. The results of the growth of the injured S. typhimurium in the various growth media is shown in FIG. 1. Modified-TSB was found to be comparable to the REVIVE media using the Biotek apparatus. Referring to Table 3, the sample grown in the modified-TSB media was found to grow faster and have more cell mass than the sample grown in the REVIVE medium after six hours of incubation indicating greater resuscitation.

Growth Inhibitors of Non-Target Microorganisms

Figure 2:
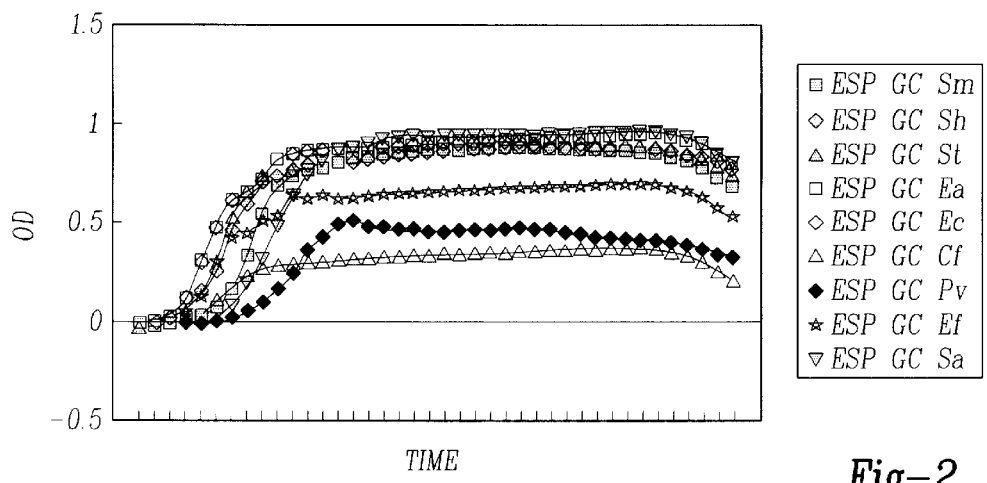
FIG. 2 is a graph illustrating the growth over time of various bacterial samples in modified-TSB media with no inhibitors added.
Figure 3:
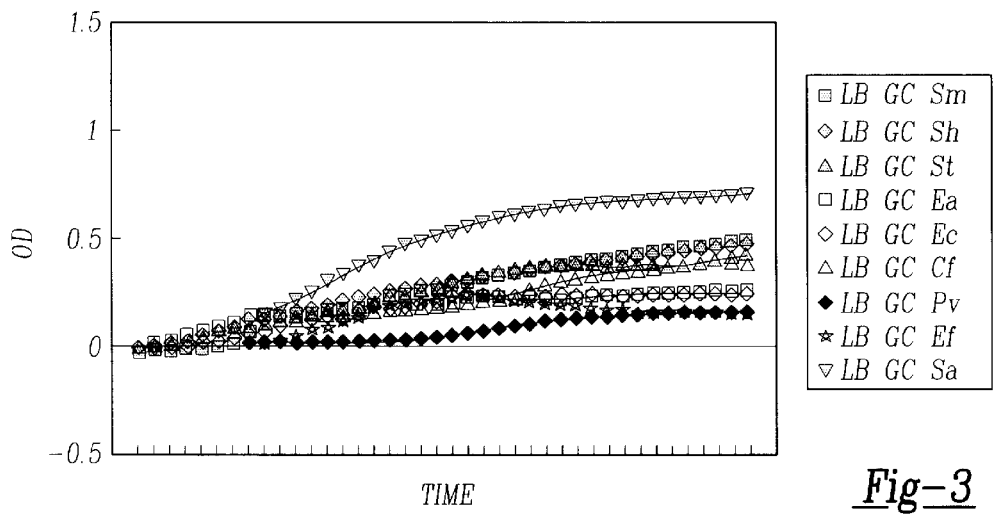
FIG. 3 illustrates the growth over time of various bacterial samples in a lactose broth control medium.

Several inhibitors were tested with three Salmonella (2 enteritidis, 1 typhimurium) and six competing organisms ((4 Grain negative (−)), 2 Gram positive (+)). All organisms were tested both with and without the inhibitor, individually, and in both modified-TSB and lactose broth (LB). Growth controls were tested without inhibitors for modified-TSB and LB as shown in FIGS. 2 and 3, respectively.

The organisms tested were S. enteritidis muenster (Sm), S. enteritidis heidelberg (Sh), S. typhimurium (St) and competing microorganisms Enterobacter aerogenes (Ea), E. coli (Ec), Citrobacter freundii (Cf), Proteus vulgaris (Pv), E. faecalis (Ef), and S. aureus (Sa).

Figure 4:
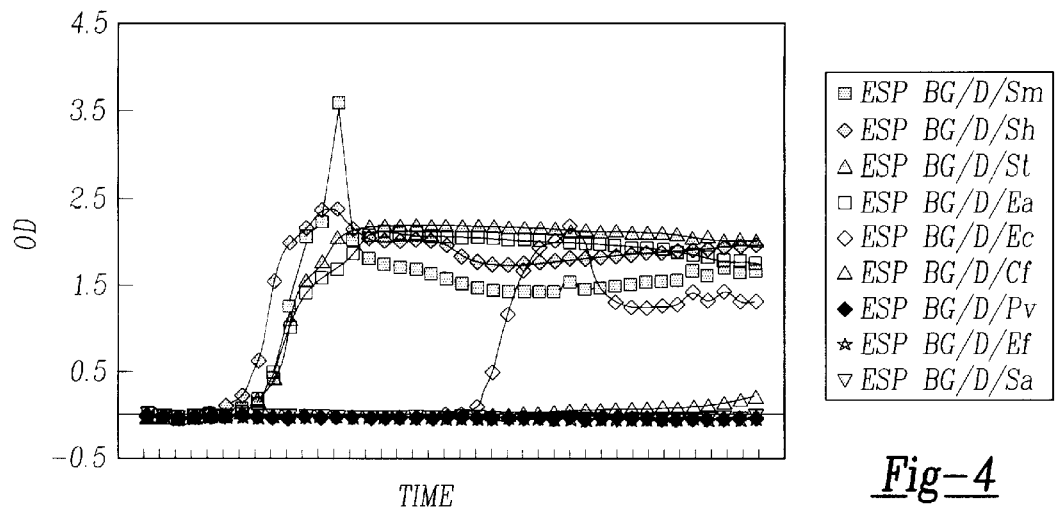
FIG. 4 is a graph illustrating the growth over time of various bacterial samples in modified-TSB media with the inhibitor combination brilliant green/deoxycholate.
Figure 5:
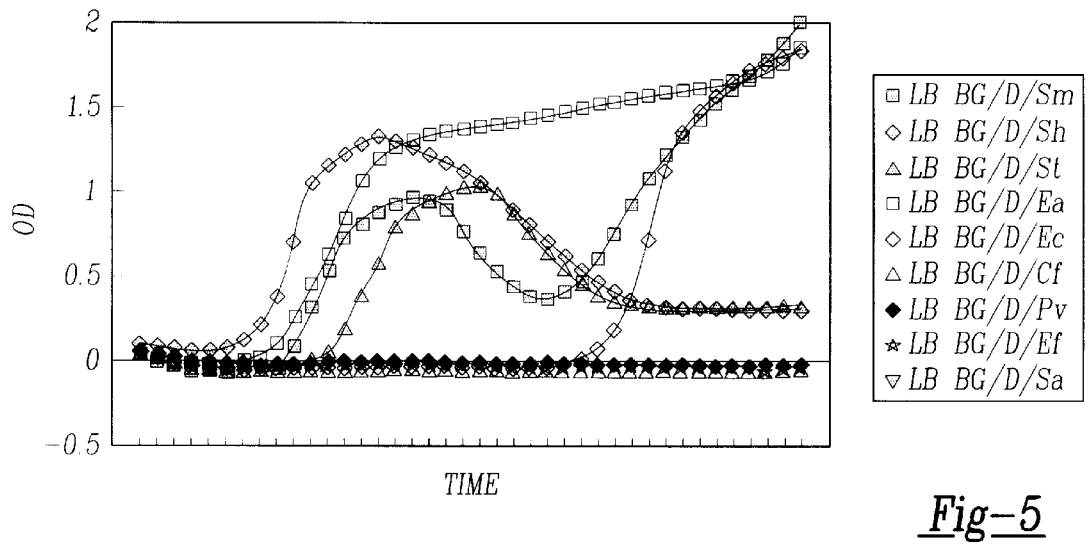
FIG. 5 is a graph illustrating the growth over time of various bacterial samples in lactose broth with the inhibitor combination brilliant green/deoxycholate.

The first inhibitor tested was deoxycholate/Brilliant Green 0.25 %/0.001%, respectively, the results shown in FIGS. 4 and 5. FIG. 3 illustrates the results of modified-TSB having no deoxycholate/Brilliant Green added thereto. The Salmonella species and the Ea grew well in the modified-TSB media with the deoxycholate/Brilliant Green inhibitor. The Ec growth was delayed. The growth of Cf. Pv, Ef, and Sa, were inhibited as shown in FIG. 4. Referring to FIG. 5, the growth of the Salmonella species and Ea in the LB with deoxycholate/Brilliant Green added thereto is illustrated in FIG. 5. The growth of Ec was delayed and the growth of Cf. Pv, Ef, and Sa, were inhibited.

Figure 6:
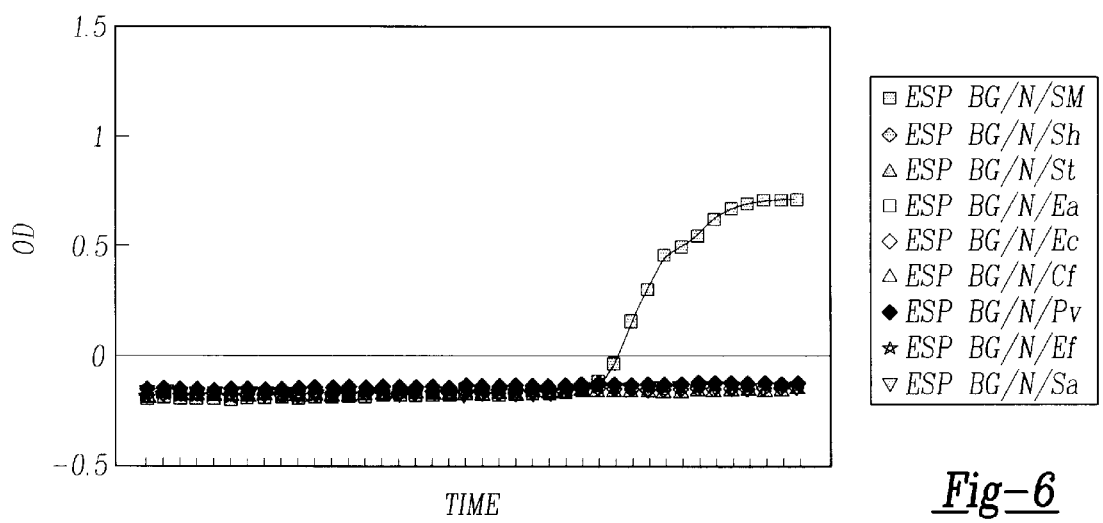
FIG. 6 is a graph illustrating the growth over time of various bacterial samples in modified-TSB with the inhibitor combination brilliant green/novobiocin.

Referring to FIG. 6, the growth of the test organisms set forth above is illustrated for modified-TSB having the inhibitor combination novobiocin/Brilliant Green (0.0001%/0.001%), respectively, added thereto. The growth of Sm was delayed and the growth of all other test organisms was inhibited. The identical experiment was performed using LB with novobiocin/Brilliant Green and the growth of all test organisms was inhibited.

Figure 7:
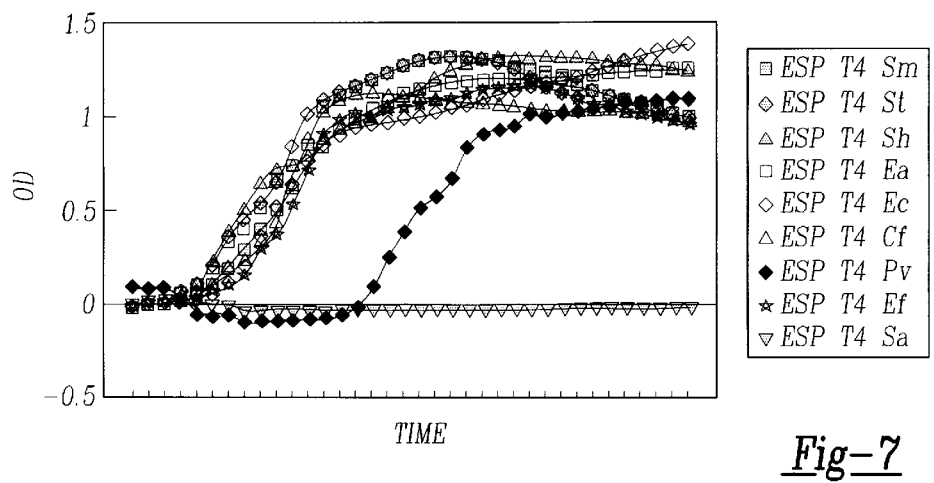
FIG. 7 is a graph illustrating the growth over time of various bacterial specimens in modified-TSB media with the inhibitor tergitol 4.
Figure 8:
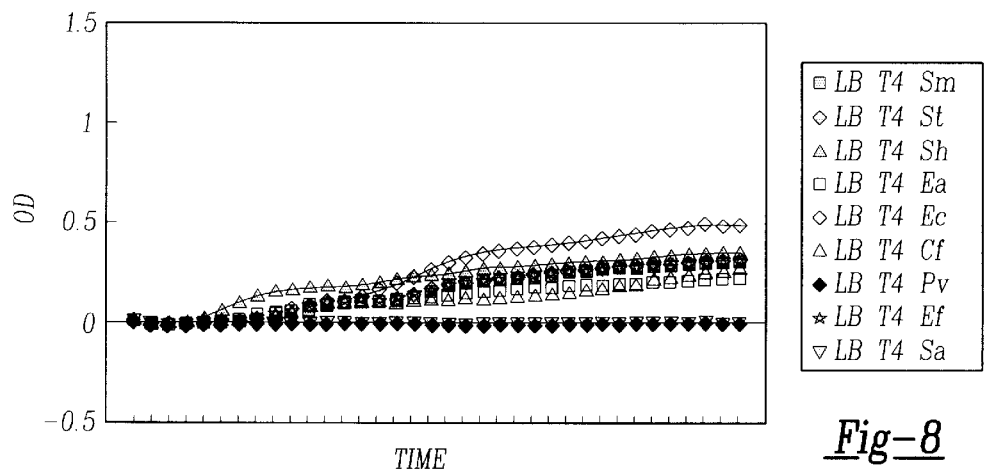
FIG. 8 is a graph illustrating the growth over time of various bacterial specimens in lactose broth with the growth inhibitor tergitol 4.

The effect of the inhibitor tergitol 4 (XLT4 Supplement, Difco Laboratories, Detroit, Mich.) at a concentration of approximately 0.046% was tested in both modified-TSB and LB in order to determine its effect on the test organisms. As shown in FIG. 7, in modified-TSB the tergitol 4 inhibited Sa growth. The growth of Pv was delayed and the other test organisms grew well. Referring to FIG. 8, the effect of the tergitol 4 in LB illustrates that the growth of Sa and Pv were inhibited while the other test organisms grew well.

Figure 9:
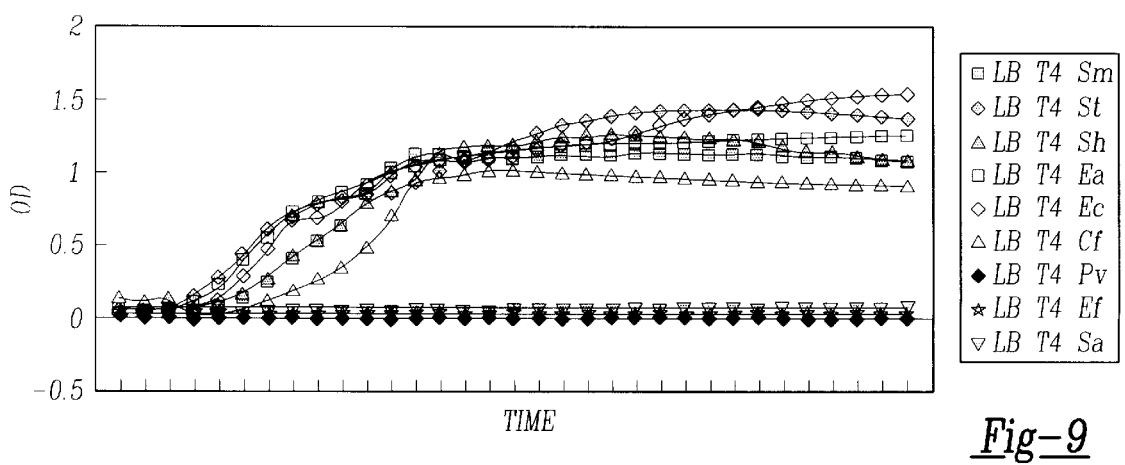
FIG. 9 is a graph illustrating the growth over time of various bacterial specimens in modified-TSB with the inhibitor combination tergitol 4/brilliant green.

The effect of the inhibitor combination tergitol 4/Brilliant Green, 0.046%/0.00 1%, respectively, in modified-TSB is illustrated in FIG. 9. The Salmonella species, Ea, and Ec, grew well in the presence of this inhibitor combination. The growth of the Cf was slightly delayed, and the growth of Pv, Ef, and Sa were inhibited.

The inhibitor combination tergitol 4/Brilliant Green in LB inhibited the growth of all of the test organisms.

Figure 10:
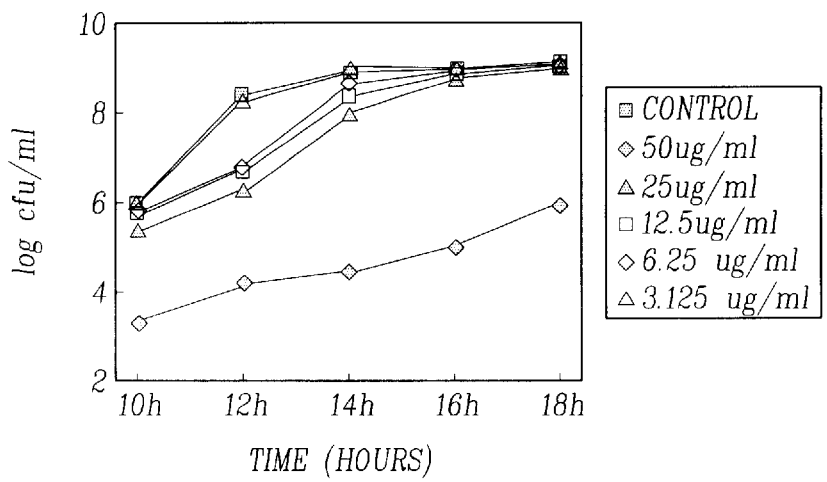
FIG. 10 is a graph illustrating the growth curve for S. typhimirium in modified-TSB media with novobiocin wherein the concentration of novobiocin was varied in order to determine its effect on growth.
Figure 11:
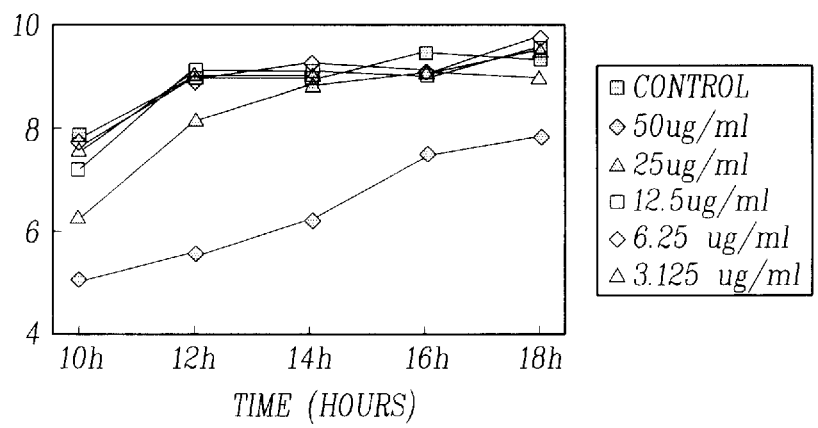
FIG. 11 is a graph illustrating the growth curve for S. brandenberg in modified-TSB media with novobiocin wherein the concentration of novobiocin was varied in order to determine its effect on the growth of the S. brandenberg.

As shown in FIGS. 10 and 11 and Tables 4 and 5, the results of experiments designed to determine both the ideal concentration of and time of administration of novobiocin in modified-TSB are illustrated. The effects of different concentrations of novobiocin ranging from 3.125–50 µg/ml on heat injured *S. typhimurium* and *S. brandenberg* were studied. Additionally, studies were also performed on combinations of Salmonella and non-Salmonella (1–10 cfu/ml of Salmonella vs. $10^4$ cfu/ml non-Salmonella) in order to determine the optimum concentration of novobiocin. It was found that at a concentration of 50 µg/ml that most gram positive organisms were inhibited and that most gram negative organisms with the exception of *C. freundii* and *E. coli* were inhibited. However, at this concentration, Salmonella were also inhibited. A concentration of approximately 25 µg/ml in modified-TSB media was found to be the concentration which inhibited gram positives and some gram negatives, while not inhibiting the growth and resuscitation of Salmonella. It was also found that the time of addition of the novobiocin was best performed at the very beginning of the test.

Biochemical Reagents-Selective Enrichment

Biochemical reaction formulations were tested using nineteen Salmonella serotypes and fourteen non-Salmonella competitors as shown in Table 6. A total of eight reactions were tested with the organisms shown in Table 6. These reactions can be divided into four separate groups:

---

1.) $H_2S$ Reaction dry strip ($H_2S$—S) vs. media ($H_2S$-M)

2.) Fermentation Reactions dulcitol (DUL)
    glucuronate (GA)
    propylene glycol (PG)

3.) Decarboxylase Reaction lysine (LYS)
        }; in modified LICNR media
    ornithine (ORN)
    arginine 4.) Enzyme Cleavage Reactions A. Chromogenic (Bromochloroindolyl) -BCI
    glucuronide
    caprylate
B. Fluorogenic (Methylumbelliferyl) -MU
    glucuronide (MUG)
    caprylate (MUCAP)

A two tube system can be utilized wherein a first tube (#1) can contain:

---

$H_2S$— strip (black) or
caprylate (fluorescence)
and a second tube (#2) can contain:

dulcitol (yellow) or
glucuronide (fluorescence) or
dulcitol (yellow).

---

These reactions were investigated as targets for presumptive identification of Salmonella. These reactions were chosen because they mostly yield positive test results for Salmonella species. Referring to Table 6, the numeric number is the sum of positive test results for each organism for the test. Most Salmonella tested positive for all tests. The highest scoring competitors were the two Citrobacters, with five positive results, however, it is noted that lysine is negative for these two samples thereby allowing for a positive distinction between the Salmonella species and the Citrobacter spp.

Example 1

Combined enrichment of Salmonella Spp. in competition with Gram negative enteric bacteria. This example illustrates an experiment performed through the enrichment step to the enhanced enrichment step. This test was also performed in order to study the effect of the addition of crystal violet (cv) to 0.1% $MgCl_2$+0.003% malachite green on the reaction media.

Materials

For heat injury of the test organisms, refer to the method and material set forth above.

modified-TSB
    (Difco, Lot #91198)
    modified-TSB media (Difco)
    sodium novobiocin (Difco $R_x$ P5670-42B)
    magnesium chloride, anhydrous (Sigma, Lot #86F-3524)
    malachite green, oxalate salt (Sigma, Lot #122H0257)
    Bacto-crystal violet (Difco, Lot #727317)
    XLD-Agar (Difco, Lot #85746JD)
    XLD-Agar Plates
    Stomacher bags (Seward Stomacher Bags, Seward Medical)
    Bacterial Strains Used: *S. typhimurium* ATCC 14028, *S. brandenberg* ATCC 6955, *E. aerogenes* ATCC 13048, *E. coli* ATCC 25922, and *H. alvei* ATCC 23280.

Methods

See heat injury methodology set forth above.

Pre-Enrichment Assay:

Heat injured *S. typhimurium* and *S. brandenberg* were serially diluted in a 1:10 dilution to a concentration of $10^{-2}$. Two stomacher bags each containing 225 ml of modified-TSB+novobiocin (25 μg/ml) was inoculated with either the *S. typhimurium* or *S. brandenberg* into two separate bags.

The competitive microflora was prepared and added as follows: a culture of each competitor in 0.5 ml McFarland's (approximately $1 \times 10^8$ cfui/ml) was serially diluted to achieve a concentration of approximately $10^5$. Approximately 33 μl of each competitor organism was added to the stomacher bag containing the Salmonella and media to achieve a final concentration of competitors of approximately $1 \times 10^4$ cfu:/225 ml. Six stomacher bags were analyzed and arranged as follows:

(1) *Salmonella typhimurium* plus competitors with crystal violet, (2) *Salmaonella brandenberg* plus competitors with crystal violet, (3) competitors alone with crystal violet, (4) *Salmonella typhimurium* plus competitors without crystal violet, (5) *Salmonella brandenberg* plus competitors without crystal violet, and (6) competitors alone without crystal violet.

All of the bags were mixed thoroughly and incubated at air approximately 35°±2° C. for approximately four hours. After four hours of incubation, selective inhibitors were added as follows: into all bags to contain crystal violet, 1 ml of a 100× stock of 0.1% crystal violet was added along with 10 ml of 20× stock of 0.0003% malachite green +0.1% $MgCl_2$. 10 ml of the 20× stock of 0.003% malachite green +0.1% $MgCl_2$ was added to all bags marked without crystal violet. The bags were then incubated for an additional eight hours after which the samples were transferred to biochemical reaction reagents as described below.

After transferring the samples, to reaction media tubes, the bags were all incubated for an additional twelve hours. Following this incubation, (twenty-four hours from start) plate counts were performed on TSA and XLD plates.

Results

Initial Inocula

*S. typhimurium*=610 c.f u./225 ml (92% heat injury)

*S. brandenberg*=101 c.f.u./225ml (91% heat injury)

Others (*E. coli*, *E. aerogenes*, and *H. alvei*) =$1.0 \times 10^4$ c.f.u./225 ml.

Twenty-two Hour Plate Counts with crystal violet

*S. typhimurium*/competitors

Salmonella=$2.2 \times 10^8$ cfu/ml

Competitors=$5.7 \times 10^8$ cfu/ml

*S. brandenberg*/competitors

Salmonella=$3.1 \times 10^8$ cfu/ml

Competitors=$7.0 \times 10^8$ cfu/ml

Example 2

Complete enrichment model of Salmonella with *E. coli E. aerogenes* and *Hafnia alvei*.

The purpose of this experiment was to determine if a dye/inhibitor system used during both the pre-enrichment stage and selective enrichment stage would have an effect on the color and fluorescence reactions utilized as negative Salmonella screens. Additionally, this experiment was performed in order to obtain population and growth information from a true model system.

Materials disodium L-cystine (Difco, P-2401-20B)

ferric ammonium citrate (Sigma, 67F-0825)

salicin (Difco, #798545)

sodium thiosulfate (Sigma, S-1648)

mannitol (Difco, 7497L)

dextrose (Difco, 709544)

yeast extract (Difco, 0127-19-9)

L-lysine HCl (Difco, P-0705-20B)

tryptone, pancreatic digest of casein #3 P-5940)

neutral red (Sigma, N-7005)

$H_2S$ strips (Difco, 1626-30-6)

MUCAP (Research Organics, 0179 M-2)

phenol red (Difco $R_x$, 5533N)

dulcitol (Sigma, D-0256)

ethyl alcohol, anhydrous (Spectrum Chemical)

sodium hydroxide hydrochloric acid caprylic acid (Sigma, C-5038)

sodium citrate (Difco, P-7260-20B)

magnesium sulfate (Sigma, M-1880)

ammonium dihydrogen phosphate (Sigma, A-1 645)

dipotassium phosphate (Difco, P-6500-20B)

sodium chloride (Difco, 7240 RX6081R magnesium sulfate (Sigma, M0250)

ferrous sulfate (Sigma, F-7002)

| Reaction Media: | |
|---|---|
| Ingredient | g/l |
| 1.) MUCAP + $H_2S$ Strip Media-citrate based | |
| magnesium sulfate | 0.2 |
| ammonium dihydrogen phosphate | 1 |
| dipotassium phosphate | 1 |
| sodium chloride | 5 |
| yeast extract | 0.3 |
| sodium citrate | 5 |
| sodium thiosulfate | 0.1 |
| pH of media | 7.83 |
| 2.) Modified LICNR Media | |
| yeast extract | 3 |
| tryptone | 5 |
| L-lysine | 10 |
| L-cystine | 0.1 |
| mannitol | 5 |
| dextrose | 1 |
| salicin | 1 |
| neutral red | 0.025 |
| pH of media | 6.2 +/- 0.2° C. @ 25° C. |

Both media 1 and 2 were prepared and dispensed in 9 ml aliquots in media tubes and autoclaved for fifteen minutes at 121 ° C.

A total of six bags were prepared and contained the modified-TSB media including Novobiocin as set forth above. The bags were inoculated with bacteria as follows:

Bag 1—St, Ec, Ea, Ha

Bag 2—Sb, Ec, Ea, Ha

Bag 3—Ec, Ea, Ha

Bag 4—St,Ec, Ea, Ha

Bag 5—Sb, Ec, Ea, Ha

Bag 6—Ec, Ea, Ha

Bags 1–3 included crystal violet. Bags 4–6 had no crystal violet added as described in the previous example.

After twelve hours of incubation including both pre-enrichment and selective enrichment, 1 ml from each bag was transferred into two reaction tubes containing: (1) MUCAP/$H_2S$ and (2) Lys decarboxylase reagents. The $H_2S$ strip was folded over the top of the media tube and sealed down with a cap. Usually, half of the length of the strip was used for each sample. The $H_2S$ strip was incorporated with the MUCAP tube only. The tubes were then incubated to facilitate the reaction for a further twelve hours. Following the twelve hour incubation, the results of the reactions were observed and a count of the bacteria present in the reaction tubes was performed.

A time line for this example is as follows:

10 A.M. inoculate bags with injured Salmonella plus competitors

2 P.M. add inhibitors

10 P.M. transfer to biochemical reactions

10 A.M. read biochemical reactions for positive results

Note: The reactions were read at 8:30 A.M.=22.5 hours for this experiment and at twenty-four hours for Lys.

Procedure For MUCAP Test Results

1.) The samples were incubated in citrate broth with sodium thiosulfate for ten to twelve hours;

2.) A 1 ml aliquot from the sample was transferred to a separate glass reaction tube;

3.) A 1% MUCAP stock solution was prepared;

4.) A 1 μl loopful of stock MUCAP solution was added to the 1 ml aliquot of sample; and 5.) The fluorescence reaction was allowed to develop and was read every five minutes to at least fifteen minutes and was observed with a Woods lamp.

The results for this example are set forth in Table 7.

The MUCAP reagent can either be added directly to the sample by adding an aliquot of MUCAP solution or can be added by first disposing the MUCAP reagent onto a solid support, such as a paper strip. The concentration of the methylumbelliferyl caprylate in the ethyl acetate can range from approximately 0.05% to 10%. The preferred concentration of the methylumbelliferyl caprylate in the ethyl acetate is approximately 0.1 %.

A dilution of 50 μl of MUCAP reagent dissolved in ethyl acetate can be added to 5 ml of media. Additionally, the reagent can be added in a dry state via an impregnated strip and then the strip can be added to the media in order to introduce the MUCAP reagent as set forth below in Example 3. Results for use in the liquid form is the same as those shown in Table 7. Previously, the MUCAP reagent could not be used in liquid form as it had a tendency to precipitate from solution. However, as used herein, the MUCAP reagent dissolved in ethyl acetate can be used either directly in liquid form or the MUCAP reagent dissolved in ethyl acetate can be dried onto a solid substrate and the utilized, in both cases the precipitation has been eliminated.

TABLE 7

|        | 1   | 2   | 3 | 4   | 5   | 6 |
|--------|-----|-----|---|-----|-----|---|
| MUCAP* | +++ | +++ | − | +++ | +++ | − |
| $H_2S$ | +   | +   | − | +   | +   | − |
| Lys    | −   | −   | − | −   | −   | − |

TABLE 7-continued

|   |   |   |   |   |   |
|---|---|---|---|---|---|
| 1 | 2 | 3 | 4 | 5 | 6 |

*after 15 minutes of development
$H_2S$ Results:
+ = any black precipitate formed on strip
− = white strip
Lysine Results:
+ = yellow
− = remains red
MUCAP Results:
− = media background or equal
+ = very weak fluorescence above background
++ = fluorescence stronger, may be determined positive without reference
+++ = good, bright positive
++++ = strong fluorescence The MUCAP results were best observed after at least fifteen minutes of incubation.

$H_2S$ results

St samples were positive after nineteen hours.

Sb samples were positive after 20.5 hours.

MUCAP +NaOH Results

After 22.5 hours, 10 μl of 0.1N NaOH was added to a 1 ml test aliquot of each sample in order to increase the observed fluorescence in the tube. The results of the addition of the sodium hydroxide to the MUCAP media are shown in Table 8.

TABLE 8

| MUCAP w/NaOH after fifteen minutes. | | | | | | |
|---|---|---|---|---|---|---|
| Sample | 1 | 2 | 3 | 4 | 5 | 6 |
|  | ++++ | ++++ | + | ++++ | ++++ | + |

It was found that the fluorescence was increased with very little effect on the negative samples (3 and 6) which contained only competitors.

Lysine Results

After thirty hours of incubation, the lysine test became differential as shown in Table 9.

TABLE 9

| 1 | 2 | 3 | 4 | 5 | 6 |
|---|---|---|---|---|---|
| +yel | +yel | −red | +yel | +yel | −red |

Bacterial counts were taken at 22.5 hours in the MUCAP/$H_2S$ tubes. Samples 1, 2, 4, and 5 were counted on XLD media and samples 3 and 6 were counted on TSA media. The results of these counts is set forth in Table 10.

TABLE 10

|  | 1 | 2 | 3 | 4 | 5 | 6 |
|---|---|---|---|---|---|---|
| Salmonella | $9.5 \times 10^8$ | $5.5 \times 10^8$ | — | $8.9 \times 10^8$ | $9.1 \times 10^8$ | — |
| Competitors | NT | NT | $<10^5$ | NT | NT | $7.7 \times 10^8$ |

NT: not tested

It was noted that the competitors in sample 3 (bag 3) were reduced to less than $10^5$ cfu/ml from the enrichment procedure.

As shown in Table 2, as compared with conventional methods of Salmonella testing, the method of the present invention described above allows for the rapid detection of target microorganisms is a sample which can contain non-target organisms as well as target organisms by specifically tailoring and/or modifying biochemical assays so that they can be performed on a potentially mixed culture thereby greatly reducing the time required for obtaining useful test results.

Example 3

In order to evaluate the performance of the rapid microorganism detection system of the present invention, samples were tested in different conditions. First, a sample was tested which was spiked with *S. typhimurium* and a sample without being spiked with the *S. typhimurium*. A four hour pre-enrichment @ 37° C. followed by eighteen hours of selective inhibition at 35° C.±2° C. was performed. Lysine, MUCAP, and $H_2S$ tests were performed for up to six hours @ 42° C. for Salmonella detection.

Material
- Chicken—Tyson
- Shrimp—shell—on
- Red dye—McCormick
- Dried egg yolk—Sigma E-0625
- Eggs—large, AA
- novobiocin—Difco 48580JA
- TSA (Difco 97897)
- Hektoen Enteric Agar
- Stomacher Bags
- Stomacher Apparatus—Tekmar Lab Blender
- Lysine-6 for Lysine reaction
- Ethyl Acetate (Sigma 27, 052-0)
- 0.5% peptone for $H_2S$ reaction
- MUCAP strips
- $MgCl_2$ (anhydrous)—Sigma M-8266
- Malachite green—Sigma M-6880
- Crystal violet—Difco 727317
- *S. typhimurium* ATCC 14028
- TSB (Difco 97214)
- 5 0.85% NaCl - Difco 94669
- Modified-TSB—Difco 91198
- $H_2S$ strips—Difco 95855 JB
- Commercial Bleach—Clorox
- SDS—J. T. Baker (L050-5)
- sterile containers
- sterile scalpels
- sterile glassware
- pipets, tips, etc.

Methods

Day-1

(1) Modified-TSB: 3 liters total:

98.4 g of modified-TSB powder was dissolved in 3 liters of water which was gently heated. The mixture was autoclaved for fifteen minutes @ 121° C., 15 lbs pressure and allowed to cool overnight to room temperature.

(2) Selective inhibitors: 200 ml total:

4.0 g of $MgCl_2$ was placed into 200 ml of distilled water and dissolved completely. 0.12 g of malachite green was added to the $MgCl_2$ mixture 0.02 g of crystal violet was added to the mixture. The mixture was heated gently to dissolve the solids completely. The mixture was allowed to cool to room temperature and was filter sterilized using a 0.22 μm filter.

(3) *S. typhimurium*: A sub-culture was prepared in TSB and incubated overnight @ 37° C. A 100 μl sample of a $10^{-3}$ dilution from an injured culture (injured as described above) was added to each bag labeled "spiked."

(4) MUCAP strips: A 0.1% solution of MUCAP was prepared in ethyl acetate. Blank filter paper strips were dipped into the 0.1% stock solution and were completely air dried.

(5) Lysine-6 for lysine reaction:
- Magnesium sulfate—0.1 g
- Ammonium phosphate monobasic—0.5 g
- Potassium phosphate dibasic—0.5 g
- NaCl—2.5 g
- Yeast Extract—0.15 g
- Lysine HCl—5.0 g
- Brown Cresol Purple—2.5 ml of 0.2% stock
- Lactose—1.25 g
- Sucrose—1.25 g The above were dissolved in 1 L of distilled water, pH was adjusted to 5.1 and sterilized at 121 ° C. and 15 lbs pressure for 15 minutes. Samples were dispensed into sterile 5 ml tubes.

(6) 0.5%peptone:

Into 100 ml D1 $H_2O$, 0.5 g of peptone was dissolved and autoclave at 121° C. and 15 lbs pressure for 15 minutes. The solution was allowed to cool to room temperature and 5 ml samples were dispensed into sterile tubes.

(7) Hektoen Enteric Agar: A one liter volume was prepared according to the manufacturers' instructions and stored overnight at room temperature.

Day-2

(1) Stomacher Bags 225 ml of modified-TSB was dispensed into sterile stomacher bags and labeled as follows:

| | |
|---|---|
| 1. Dried egg yolk (spiked) | 6. Dried Egg Yolk (unspiked) |
| 2. Eggs (spiked) | 7. Eggs (unspiked) |
| 3. Chicken (spiked) | 8. Chicken (unspiked) |
| 4. Shrimp (spiked) | 9. Shrimp (unspiked) |
| 5. Dye (spiked) | 10. Dye (unspiked) |
| | 11. Control (spiked, no meat) |

(2) Eggs

A one liter wash solution was prepared as follows:

One gram of SDS was added to 992 ml of $H_2O$ and 8 ml of commercial bleach was added.

The eggs used in the experiment were washed with a stiff brush and allowed to drain. The washed eggs were allowed to soak for thirty minutes in the SDS-bleach solution. The yolks were aseptically removed and twenty-five grams of each yolk was placed into the appropriately labeled stomacher bags. The bags were stomached for approximately two minutes using the Tekmar stomacher. A one milliliter aliquot was removed for pH test purposes. Another one milliliter aliquot was removed for a serial dilution in saline tubes of $10^{-2}$ and $10^{-3}$ dilutions. One milliliter of $10^{-2}$ and $10^{-3}$ were plated into empty sterile petri dishes and approximately twenty milliliters of liquid plate count agar was poured into the Petri dishes and was allowed to solidify. The plates were then incubated for 48 hours @ 35° C.±2° C.

(3) Chicken

Two samples of approximately 25 g of slashed chicken were aseptically weighed-out. The samples were placed into stomacher bags and were stomached for approximately two minutes. The stomached material was then sampled and plated as described in (2).

(4) Dried Egg Yolk

Two samples of approximately 25 g of dried egg yolk were aseptically weighed-out and placed in stomacher bags. The samples were stomached and aliquots were removed for pH testing purposes and plating purposes as set forth in (2).

(5) Shrimp

Two samples of approximately 25 g of shrimp slashed in half were aseptically weighed-out and transferred into sterile stomacher bags containing modified-TSB. The samples were handled as described in (2) above.

(6) Novobiocin

Lyophilized novobiocin was removed from storage @ 4° C. and allowed to equilibrate to room temperature. Each vial of lyophilized novobiocin contained 20 mg of novobiocin. Sterile distilled water (3.55 ml) was aseptically injected into each vial to obtain a stock solution of 5.63 mg/ml. One milliliter of novobiocin stock solution was aseptically added into each stomacher bag including the stomacher bag labeled as control (bag 11) to achieve a final concentration of 25 µg/ml. Following the addition of the novobiocin into each stomacher bag, the contents of each bag was mixed by vigorous shaking in order to distribute the novobiocin throughout the mixture.

(7) Plate Counts at Time Zero ($T_0$)

100 µl samples of inoculum from the $10^{-2}$ and $10^{-3}$ dilutions were plated onto Hektoen Enteric Media as well as onto TSA plates. The s plates were then dried for fifteen minutes under laminar flow and incubated for forty-eight hours @ 35° C.±2° C. Table 7 illustrates the results of the plate counts.

(8) Red Dye 10 ml of dye was added into 225 ml modified-TSB. The procedure as outlined in (2) detailed above was then followed.

(9) Pre-enrichment

The stomacher bags (with samples and control) were incubated @ 35° C.±2° C. for four hours. Plate counts were taken at $T_4$ and the results are shown in Table 8.

(10) Selective Inhibition

The eleven bags were removed from incubation @ 35° C.±2° C. after four hours. 10ml of selective inhibitor was added and mixed. The bags were then incubated @ 35° C.±2° C. overnight.

Day-3

(11) Biochemical Reactions (a) Lysine:

5 ml of Lysine-6 was dispensed into sterile tubes.

50 µl (1:100 dilution) from each bag was added to a separate tube containing Lysine-6. All of the tubes, along with a negative control, were incubated @ 42° C. for up to six hours. Each tube was read every hour. The results are shown in Table 11.

(b) $H_2S$:

5 ml of 0.5% peptone was dispensed into sterile tubes.

100 µl from each bag was dispensed into separate tubes containing 0.5% peptone.

An $H_2S$ strip was hung into each tube along with a negative control tube. The tubes were incubated at 42° C. for up to six hours. The results are shown in Table 12.

(c) MUCAP:

5 ml of Lysine-6 was dispensed into sterile tubes.

100 µl of test material from each bag was placed into separate tubes containing the Lysine-6.

A MUCAP strip was hung into each tube including the negative control tube, the tubes were not inverted and were allowed to incubate @ 42° C. for up to six hours. The tubes were then momentarily inverted and any changes were read after five, ten, and fifteen minutes at room temperature. The results are shown in Table 13.

(12) Interpretation of Biochemical Reactions (a) Lysine: A change from yellow coloration to purple coloration indicated a positive reaction.

(b) $H_2S$: Blackening of the $H_2S$ strip indicated a positive reaction.

(c) MUCAP: Fluorescence at long wavelength U.V. light of 1+ or better indicated a positive reaction.

(13) Plate Counts at $T_{22}$ (a) $T_{22}$ (22 hours post inoculation): Following overnight incubation with the selective inhibitors, material from each stomacher bag was diluted into saline blanks ($10^{-1}$, $10^{-2}$, and $10^{-3}$). 50 µl of $10^{-2}$ and $10^{-3}$ were plated onto TSA and HE plates. The plates were incubated at 35° C.±2° C. overnight to determine if S. typhimurium or any other contaminant had broken through. The results are shown in Table 9 where (TNTC) indicates that the colonies were too numerous to count.

(b) $T_{27}$ (27 hours post incubation): After biochemical reaction with lysine had turned positive (if not, after six hours of incubation @ 42° C.) a loopful of reaction mixture was plated onto HE plates and incubated overnight at 35° C.±2° C. and was then observed for colony characteristics. The results are shown in Table 10.

RESULTS (1) pH of the sample foods in modified-TSB (following stomaching):

| Dried Egg Yolk | 6.8 |
|---|---|
| Egg Yellows | 7.0 |
| Shrimp | 7.22 |
| Chicken | 6.68 |
| Dye | 7.21 |
| Control (modified-TSB only) | 7.22 |

(2) Percent injury to *S. typhimurium* culture:

The percent injury was calculated as previously described and was 90.3%.

(3) The $T_0$ plate counts from the stomached samples are shown in Table 7.

CONCLUSIONS

At time zero ($T_0$), none of the samples showed any typical colonies on HE agar (see Table 7). However, the chicken and shrimp samples showed 30 c.f.u./ml at $10^{-2}$ and colonies too numerous to count (TNTC) at the $10^{-2}$ dilution on TSA suggesting contamination.

After four hours of pre-enrichment, the following was observed on TSA plates (see Table 8):

| Dried Egg Yolk - spiked | 20 c.f.u./ml of $10^{-2}$ dilution |
|---|---|
| Chicken - spiked | 20 c.f.u./ml of $10^{-2}$ dilution |
| Shrimp - spiked | 220 c.f.u./ml of $10^{-2}$ dilution |
| Chicken - unspiked | 20 c.fu./ml of $10^{-2}$ dilution |
| Shrimp - unspiked | 240 c.f.u./ml of $10^{-2}$ dilution |

None of the other bags exhibited any growth after four hours of incubation.

Referring to Table 9, after a total of twenty-two (22) hours of incubation ($T_{22}$), it was observed that on TSA, colonies too numerous to count were obtained from samples other than unspiked egg yolk and dye. This finding indicated that in both spiked and unspiked samples, organisms had a chance to grow and could break through, i.e., the bacterial concentration reaches a population $>1 \times 10^6$ cfu/ml. The egg yolks and dye were found to be sterile and remained sterile throughout the testing period. Following plating on HE agar, dried egg yolk-spiked showed blue-green colonies indicating the presence of Salmonella (see Table 10). Egg yolk-spiked showed similar results. From chicken-spiked and shrimp-spiked, colonies were isolated that were salmon colored having bile precipitation. These colonies could possibly have been E. coli. The dye-spiked sample showed typical Salmonella colonies on HE plates. Dried egg yolk-unspiked showed typical Salmonella colonies on HE plates indicating that dried egg yolk probably had some Salmonella contamination. Egg yolk-unspiked and dye remained sterile throughout the entire testing period. Chicken-unspiked was found to contain some contaminants, possibly E. coli which appeared salmon colored with bile precipitation. Shrimp-unspiked was found to contain many salmon colored colonies along with a few Salmonella-type colonies on HE agar. The positive control (spiked) was found to contain many Salmonella appearing colonies on HE agar.

Colonies from inocula from biochemical reaction tubes after six hours @ 42° C. appeared as following:

Dried Egg Yolk-spiked, egg yolk-spiked, dye-spiked, dried egg yolk-unspiked, and the control samples were found to have blue-green colonies with black centers indicating Salmonella. Chicken-spiked and shrimp-spiked showed salmon colored colonies with bile precipitation indicating the presence of a contaminant, possibly E. coli. Egg yolk-unspiked and dye-unspiked showed no growth, indicating sterility. Chicken-unspiked was found to be positive for the presence of a contaminant, possibly E. coli. Shrimp-unspiked was found to have a mixture of contaminants as well as Salmonella-like colonies. The positive control was found to contain only Salmonella-appearing colonies.

Biochemical Reactions:

Referring to Table 14, dried egg yolk-spiked was found to be positive for reactions indicative of Salmonella. This result was expected and was believed to be a true positive result. Egg yolk-spiked tested positive for the presence of Salmonella. Chicken-spiked illicited a positive biochemical profile for the presence of Salmonella. Shrimp-spiked illustrated a discrepancy which was due to the fact that both the lysine and MUCAP reactions were negative for the presence of Salmonella. Dye-spiked was unable to be determined due to the fact that both the lysine and MUCAP reactions were difficult to read due to the dark red color of the reaction media. The $H_2S$ test was found to be positive for the presence of Salmonella. Dried egg yolk-unspiked tested negative utilizing the biochemical profile, however, on HE agar, Salmonella-like colonies were present which could indicate the presence of Salmonella or other contaminants. Egg yolk-unspiked was found to produce a true negative biochemical profile. Chicken-unspiked demonstrated a weakly positive biochemical profile. This result coupled with the fact that contaminants were isolated on HE agar indicated that the biochemical profile for chicken-unspiked was a true negative result. Shrimp-unspiked produced a discrepancy due to the fact that the biochemical results were positive indicating contamination with Salmonella. Dye-unspiked remained sterile and did not produce any colonies throughout the entire test. The control tubes illustrated a strong positive biochemical profile for the presence of Salmonella which was indicative of a true positive result.

These results, including the discrepancies for both shrimp-spiked and shrimp-unspiked, demonstrated that the rapid microorganism detection method of the present invention yielded definitive results within a twenty-eight hour total testing period.

Example 4

This example illustrates an experiment performed in order to evaluate the performance of the rapid microorganism detection method of the present invention by testing spiked (with S. typhimurium) and unspiked chicken, shrimp, non-fat dry milk, whole black pepper, ground pork, ground beef, and milk chocolate.

Materials non-fat dry milk—Saco Mix'n Drink whole black pepper—McCormick ground pork sausage ground beef milk chocolate—Hershey's Milk Chocolate Bar TSI Agar—Difco 72853 JG The remaining materials were as listed in Example 3.

Methods

The methods were carried out as described in Example 3.

Day-2

(1) Stomacher Bags: 225 ml of modified-TSB w/o minerals was dispensed into sterile stomacher bags and labeled as follows:

| Spiked | Unspiked |
|---|---|
| 1. Chicken | 8. Chicken |
| 2. Shrimp | 9. Shrimp |
| 3. Dry Milk | 10. Dry Milk |
| 4. Whole Black Peppers | 11. Whole Black Peppers |
| 5. Ground Pork Sausage | 12. Ground Pork Sausage |
| 6. Ground Beef | 13. Ground Beef |
| 7. Milk Chocolate | 14. Milk Chocolate |
|  | 15. Control |

(2) 25 g of test material was weighted into stomacher bags labeled as in (1).

(3) Novobiocin: As described above in Example 3.

(4) Plate Counts at Time Zero ($T_0$):

100 µl of inoculum from the $10^{-2}$ and $10^{-3}$ dilutions were plated onto Hektoen Enteric media as well as TSA plates. The plates were then dried for fifteen minutes under laminar flow and incubated for forty-eight hours @ 35° C.±2° C. The results are shown in Table 15.

(5) Pre-enrichment:

The stomacher bags (with samples and control) were incubated @ 35° C.±2° C. for four hours.

(6) Selective Inhibition:

The bags were removed from incubation @ 35° C.±2° C. after four hours in incubation. 10 ml of selective inhibitor was added and mixed. The bags were then placed into the incubator @ 35° C.±2° C. for overnight incubation. Plate counts were taken and $T_4$ and the results are shown in Table 16.

(7) Biochemical Reactions:

(a) Lysine:

Performed as described above. Results are shown in Table 17.

(b) $H_2S$:

Performed as described above. Results are shown in Table 18.

c) MUCAP:

Performed as described above. Results are shown in Table 20.

(8) Interpretation of Results:

Lysine: Change from yellow color to purple color indicated a positive test result; change from yellow color to grey color indicated a weak positive test result.

H₂S: Slight blackening the strips indicated a weak positive; moderate blackening indicated a positive test.

MUCAP: 1+ or higher in fluorescence indicated a positive test result.

(9) Plating on HE and TSI at $T_{22}$:

Hektoen Enteric Agar: Blue-green colonies with black centers indicated Salmonella; orange colonies with bile precipitation indicated contaminants. The results are shown in Tables 21 and 22.

TSI Slants: Alkaline slant, black butt, and gas production indicated the presence of Salmonella; yellow slant and butt, and gas production indicated the presence of *E. coli*; and black slant and butt, some yellow color (acid slant) indicated cross-contamination between Salmonella and a contaminant. The results are shown in Tables 21 and 22.

RESULTS (1) pH of test material in modified-TSB after two minutes of stomaching:

| | |
|---|---|
| control | 7.3 |
| chicken | 6.82 |
| shrimp | 7.34 |
| dry milk | 6.79 |
| pepper | 7.22 |
| pork sausage | 6.86 |
| ground beef | 6.84 |
| milk chocolate | 6.96 |

(2) Number of organisms per bag (spiked samples only):

100 μl if $10^{-4}$ injured culture: 1 c.f.u. on a TSA plate yielded approximately 1 c.f.u./bag at $T_0$.

$T_0$ on HE plates:

50 μl of $10^{-2}$ and $10^{-3}$ dilution were plated onto HE plates. The results are set forth in Table 15.

CONCLUSIONS

Referring to the results depicted on Table 19, dry milk, whole black pepper, and milk chocolate (all unspiked), had true negative test results. All of the seven spiked samples had a positive test for Salmonella. Chicken, shrimp, ground pork sausage, and ground beef (all unspiked) were all found to test positive for Salmonella indicating that these products may have been contaminated with Salmonella or Salmonella-like organisms that yielded positive biochemical test profiles for the presence of Salmonella.

In all of the positive test results for the presence of Salmonella, blue-green colonies were observed either at twenty-two hours or twenty-eight hours on Hektoen Enteric Agar, which is indicative of Salmonella-like organisms.

TSI Slant results from these colonies confirmed the presence of Salmonella. However, $10^{-2}$ and $10^{-3}$ dilutions were found to have overcrowding of colonies on HE agar. In some cases the overcrowding masked the presence of Salmonella.

These results indicate that even when an inoculum of only one cell or colony forming unit (c.f.u.) of *S. typhimurium* was inoculated into food samples, that definitive test results were obtained in less time than that required by prior art methods.

Throughout this application various publications are referenced by citation and number. Full citations for the publication are listed below. The disclosure of these publications in their entireties are hereby incorporated by reference into this application in order to more fully describe the state of the art to which this invention pertains.

The invention has been described in an illustrative manner, and it is to be understood the terminology used is intended to be in the nature of description rather than of limitation.

Obviously, many modifications and variations of the present invention are possible in light of the above teachings. Therefore, it is to be understood that within the scope of the appended claims, the invention may be practiced otherwise than as specifically described.

TABLE 1

| SYSTEM NAME | PRE-ENRICHMENT INC. TIME/TEMP | SELECTIVE STEP INC. TIME/TEMP | ADDITIONAL STEP INC. TIME/TEMP | ASSAY FORMAT | TOTAL TIME | SENSITIVITY/ SPECIFICITY |
|---|---|---|---|---|---|---|
| AOAC | LACTOSE BROTH TRYPTONE SOYA BROTH NUTRIENT BROTH 24h/3SC | SELENITE CYSTINE BROTH (SC) OR TETRATHIONATE BROTH (TT) 24h/33C | NONE | PLATING MEDIA-BRILLIANT GREEN AGAR HEKTOEN AGAR XLD AGAR 24h/35C BISMUTH SULFITE AGAR 48h/35C | 3 DAYS 4 DAYS | 100% |
| ISO | BUFFERED PEPTONE WATER (BPW) 18h/35–37C | RAPPAPORT-VASSILIADIS BROTH (RV) 8h/42C OR SC BROTH 8h/35C | NONE | PLATING MEDIA-BRILLIANT GREEN AGAR 24h/35C | 3 DAYS | 100% |
| SALMONELLA-TEK ORGANON-TEKNIKA CORPORATION | LACTOSE BROTH NUTRIENT BROTH 24+/− 2h/35C | TT BROTH 18–24h/42C AND SC BROTH 18–24h/35C | POST-ENRICHMENT: TRANSFER FROM SELECTIVE MEDIUM TO M-BROTH WITH 10 ug/ml NOVOBIOCIN 16–20h/35C | ELISA-MONOCLONAL ANTIBODIES APPROX. 2 hrs | 4 DAYS | 96.5% 89.3% |
| TECRA INTERNATIONAL BIOPRODUCTS, INC | NON-INHIBITORY BROTH 18–22h/35C | TT BROTH AND SC BROTH 6–8h/35C | POST-ENRICHMENT: TRANSFER FROM SELECTIVE MEDIUM TO M-BROTH 16–20h/35C | ELISA-SALMONELLA VISUAL IMMUNOASSAY APPROX. 2 hrs | 3 DAYS | 98.6% 96.1% |
| TECRA UNIQUE | RAW FLESH FOODS: | NONE- | NONE | ELISA- | 2 DAYS | |

TABLE 1-continued

| SYSTEM NAME | PRE-ENRICHMENT INC. TIME/TEMP | SELECTIVE STEP INC. TIME/TEMP | ADDITIONAL STEP INC. TIME/TEMP | ASSAY FORMAT | TOTAL TIME | SENSITIVITY/ SPECIFICITY |
|---|---|---|---|---|---|---|
| INTERNATIONAL BIOPRODUCTS, INC | MODIFIED BPW WITH TERGITOL-7 OTHER FOODS: MODIFIED BPW 16h/35C | SELECTIVE THROUGH DIPSTICK | | DIPSTICK ASSAY APPROX. 6 hrs | | |
| TECRA SALMONELLA IMMUNOCAPTURE INTERNATIONAL BIOPRODUCTS, INC. | MODIFIED BPW WITH EXTRA PHOSPHATE BUFFER MIN 16h/35–37C | IMMUNOENRICHMENT:1 TUBE MODIFIED BPW 1 TUBE OF M-BROTH INCUBATE WITH DIPSTICKS AT ROOM TEMP FOR A MINUMUM OF 20 MIN | NONE | ELISA- DIPSTICK ASSAY APPROX. 6 hrs | 2 DAYS | |
| PATH STIK LUMAC BV | BP WATER OR BP WATER WITH BRILLIANT GREEN 16–24H/37C | RV BROTH 16–24h/42C | POST-ENRICHMENT: BP WATER 6–8h/37C | ELISA- DIPSTICK ASSAY 10 MINUTES | 3 DAYS | 93.0% 96.4% |
| 1–2 TEST BIOCONTROL SYSTEMS, INC | LOW MICRO LOAD: NONINHIBITORY BROTH 24h/35C HIGH MICRO LOAD: PRE-ENRICH AS IN BAM 24h/35C | NONE HIGH MICRO LOAD: IODINE ACTIVATED TETRATHIONATE BRILLIANT GREEN BROTH 8h/42C | NONE | IMMUNODIFFUSION- WHITE BAND OF PPT RESULTS FROM IMMOBILIZATION OF MOTILE SALMONELLA THROUGH SEMI- SOLID MEDIUM 16–50h/35C | 3 DAYS | 85– 100% 100% |
| BIO MERIEUX VIDAS BIO MERIEUX MODIFIED ISO METHOD | BP WATER 18h/35–37C | RV MEDIA 6–8h/42C AND SC BROTH 6–8h/35–37C | POST-ENRICHMENT: TRANSFER FROM SELECTIVE MEDIUM TO M-BROTH 18h/42C | ELFA- ENZYME-LINKED FLUORESCENT IMMUNO/ASSAY 45 MINUTES | 3 DAYS | |
| MODIFIED BAM METHOD | NON-SELECTIVE MEDIUM 18h/35–37C | TT BROTH 6–8h/42C AND SC BROTH 6–8h/35–37C | | | | |
| GENE TRAK GENE TRAK SYSTEMS | RAW MEATS: LACTOSE BROTH 22–24h/35C OTHER FOODS: BAM/AOAC METHOD 22–24h/35C | SC BROTH 16–18h/35C TT BROTH AND SC BROTH 6h/35C | POST-ENRICHMENT: TRANSFER FROM SELECTIVE MEDIUM TO GRAM-NEGATIVE BROTH 12–18h/35C | NUCLEIC ACID- BASED ASSAY APPROX. 2hrs | RAW MEATS: 4 DAYS OTHER FOODS: 3 DAYS | 98.5% 97.5% |
| DYNABEAD DYNAL AS | BP WATER 16–20h/37C | IMMUNOMAGNETIC SEPARATION (IMS): SELECTIVE BEADS ARE COMBINED WITH PREENRICHMENT 10 MIN AMBIENT TEMP | NONE | PLANTING MEDIA- XLD AND BGA 24h/37C | 3 DAYS | |
| MICRO-SCREEN NEOGEN CORP METHOD A | REVIVE MEDIUM 24h/37C | SC BROTH 18h/45C | NONE | CHROMATOGRAPHY COMBINED WITH GOLD LABELED IMMUNOSORBENT ASSAY (GLISA) APPROX. < 8h | 2 DAYS | |
| METHOD B | BAM METHOD LACTOSE BROTH 22–26h/37C | SC AND TT BROTH 24h/37C AND RV BROTH 24h/44C | | ISOLATION ON SELECTIVE AGAR MEDIA 24h/35C | 4 DAYS | |

TABLE 2

COMPARISON OF THE CONVENTIONAL SALMONELLA TESTING METHOD TO DIFCO'S RAPID SALMONELLA TEST

| Time | Conventional | Competitor Method-Reveal | Difco Rapid Salmonella (Automated Transfer) | Difco Rapid Salmonella (Manual Transfer) |
|---|---|---|---|---|
| Day 1 | Preenrichment: | Primary enrichment: | Primary enrichment | Primary enrichment |
|  | inoculate and | Preenrichment | Preenrichment | Preenrichment |
|  | stomach food sample in non-inhibitory media | inoculate and stomach food sample in non-inhibitory media Selective enrichment | inoculate and stomach food sample in media with mild inhibitor Selective enrichment | inoculate and stomach food sample in media with mild inhibitor Selective enrichment |
|  | incubate 24 hours | add highly selective inhibitors at 4 hours to preenrichment | add highly selective inhibitors at 4 hours to preenrichment Secondary enrichment: transfer aliquot to reaction media at 12 hours via automated device | add highly selective inhibitors at 4 hours to preenrichment Secondary enrichment: transfer aliquot to reaction me at 24 hours via manual transfer |
| Day 2 | Selective | Detection: | Analyze reactions: | Analyze reactions: |
|  | enrichment: | immunoassay | eliminate 70–90% | eliminate 70–90% negative |
|  | transfer 1 ml aliquot of | all samples need to be tested | negative samples from detection | samples from detection Detection: |
|  | preenrichment | Move to confirmation | Detection: | immunoassay |
|  | to selective broth media incubate 24 hours | of positives | immunoassay Move to confirmation of positives | Move to confirmation of positives |
| Day 3 | Detection: |  |  |  |
|  | Plate all samples on selective agar from selective enrichment broth to obtain pure cultures incubate 24 hours |  |  |  |
| Day 4 | Analyze plates for suspect Salmonella colonies Move to confirmation of positives |  |  |  |

TABLE 3

SIX HOUR PLATE COUNT BEFORE TRANSFER TO BIOTEK

| BROTH | TSA | TSA + NaCl |
|---|---|---|
| REVIVE | 1.5 E + 04 | 1.5 E + 04 |
| ESP-TSB | 2.1 E + 04 | 2.1 E + 04 |
| LACTOSE | 8.6 E + 03 | 4.7 E + 03 |

TABLE 4

GROWTH OVER TIME FOR *S. TYPHIMURIUM* VARIOUS CONCENTRATIONS OF NOVOBIOCIN

| Time | Control | 50 ug/ml | 25 ug/ml | 12.5 ug/ml | 6.25 ug/ml | 3.125 ug/ml |
|---|---|---|---|---|---|---|
| 10 h | 1.0 E + 06 | 2 E + 03 | 2.3 E + 05 | 6.0 E + 05 | 6.5 E + 05 | 1.0 E + 06 |
| 12 h | 2.4 E + 08 | 1.6 E + 04 | 2.0 E + 06 | 5.4 E + 06 | 6.5 E + 06 | 1.7 E + 08 |
| 14 h | 6.9 E + 08 | 3 E + 04 | 9.1 E + 07 | 2.3 E + 08 | 4.2 E + 08 | 8.8 E + 08 |
| 16 h | 9.4 E + 08 | 1 E + 05 | 5.2 E + 08 | 7.3 E + 08 | 9.2 E + 08 | 9.6 E + 08 |
| 18 h | 1.2 E + 09 | 9 E + 05 | 8.2 E + 08 | 9.4 E + 08 | 8.7 E + 08 | 9.4 E + 08 |

TABLE 5

GROWTH OVER TIME FOR *S. BRANDENBURG* VARIOUS CONCENTRATIONS OF NOVOBIOCIN

| Time | Control | 50 ug/ml | 25 ug/ml | 12.5 ug/ml | 6.25 ug/ml | 3.125 ug/ml |
|---|---|---|---|---|---|---|
| 10 h | 7.0 E + 07 | 1.0 E + 05 | 1.8 E + 06 | 1.5 E + 07 | 5.0 E + 07 | 3.7 E + 07 |
| 12 h | 8.8 E + 08 | 3.4 E + 05 | 1.4 E + 08 | 1.2 E + 09 | 7.9 E + 08 | 8.9 E + 08 |
| 14 h | 1.0 E + 09 | 1.5 E + 06 | 6.8 E + 00 | 1.4 E + 09 | 1.9 E + 09 | 1.9 E + 09 |
| 16 h | 3.0 E + 09 | 3.3 E + 07 | 1.3 E + 09 | 1.1 E + 09 | 1.4 E + 09 | 1.2 E + 09 |
| 18 h | 2.1 E + 09 | 7.0 E + 07 | 3.2 E + 09 | 3.6 E + 09 | 5.5 E + 09 | 1.0 E + 09 |

TABLE 6

Reaction Results for Salmonella and Competitors

| | DUL | PG | GA | LYS | ORN | H2S-M | H2S-S | CIT | TOTAL |
|---|---|---|---|---|---|---|---|---|---|
| SALMONELLA | | | | | | | | | |
| *S. agona* | + | + | + | + | + | + | + | + | 8 |
| *S. anatum* | + | + | + | + | + | + | + | + | 8 |
| *S. braenderup* | + | + | + | + | + | + | + | + | 8 |
| *S. brandenburg* | + | + | + | + | + | + | + | + | 8 |
| *S. derby** | + | + | + | + | + | + | + | + | 8 |
| *S. heldelberg* | + | + | + | + | + | + | + | + | 8 |
| *S. infantis* | + | + | + | − | − | + | + | + | 6 |
| *S. kentucky* | + | + | + | + | + | + | + | + | 8 |
| *S. montevideo* | + | + | + | + | − | + | + | + | 7 |
| *S. muenchen* | + | + | + | + | + | + | + | + | 8 |
| *S. muenster* | + | + | + | + | + | + | + | + | 8 |
| *S. newport* | + | + | + | + | + | + | + | + | 8 |
| *S. oranienberg** | + | + | + | + | + | + | + | + | 8 |
| *S. pullorum* | − | − | + | + | + | + | + | + | 6 |
| *S. reading** | + | + | + | + | + | + | + | + | 8 |
| *S. schottmuelleri** | + | + | + | + | + | + | + | + | 8 |
| *S. st. paul** | + | + | + | + | + | + | + | + | 8 |
| *S. thompson** | + | + | + | + | + | + | + | + | 8 |
| *S. typhimurium* | + | + | + | + | + | + | + | + | 8 |
| COMPETITORS | | | | | | | | | |
| *Acinebacter calcoaceticui* | − | − | − | − | − | − | − | − | 0 |
| *Alcaligenes fecalis* | − | − | − | − | − | − | − | − | 0 |
| *Citrobacter diversus* | + | + | + | − | + | − | + | − | 5 |
| *Citrobacter freundii* | + | + | + | − | − | − | w+ | + | 5 |
| *Enterbacter aerogenes* | − | − | + | + | − | − | − | + | 3 |
| *Entercoccus faecalis* | − | − | − | − | − | − | − | − | 0 |
| *E. coli* | − | − | + | − | − | − | − | − | 1 |
| *Hafnia alvei* | − | − | + | − | − | + | − | − | 2 |
| *Klebsiella pneumoniae* | − | − | + | + | − | − | − | + | 3 |
| *Proteus mirabilis* | − | − | − | − | + | + | + | − | 3 |
| *Proteus vulgaris* | − | − | − | − | − | − | − | − | 0 |
| *Providencia alcalifaciens* | − | − | − | − | − | − | − | + | 1 |
| *Serratia marcescens* | − | − | − | − | − | − | − | + | 1 |
| *Staph aureus* | − | − | − | − | − | − | − | − | 0 |

*indicates new organisms tested

TABLE 7

| Sample To | 10*-2; T-24 | 10*-2; T-48 |
|---|---|---|
| # of Colonies on HE Agar: 100 ul Stomached Samples, 37° C. | | |
| DEYolk | 0 | 0 |
| Eyolk | 0 | 0 |
| Chicken | 0 | 0 |
| Shrimp | 0 | 0 |
| Dye | 0 | 0 |

| Sample | 10*-2 | 10*-3 |
|---|---|---|
| # of Colonies on PCA: 1 ml Stomached samples: T48 (incubation) | | |
| DEYolk | 0 | 0 |
| Eyolk | 0 | 0 |
| Chicken | 30 | 8 |
| Shrimp | TNTC | 129 |
| Dye | 0 | 0 |

TABLE 8

T-4 After four hours of pre-enrichment

| | 24 HOUR | | | | 48 HOURS | | | |
|---|---|---|---|---|---|---|---|---|
| Media | TSA | TSA | HE | HE | TSA | TSA | HE | HE |
| Sample | 10*-2 | 10*-3 | 10*-2 | 10*-3 | 10*-2 | 10*-3 | 10*-2 | 10*- |
| DEYolk-S | 20 c.f.u./ml | 0 | 0 | 0 | 1 | 0 | 0 | 0 |
| EYolk-S | 0 | 0 | 0 | 0 | 0 | 0 | 0 | 0 |
| Chicken-S | 20 c.f.u./ml | 0 | 0 | 0 | 1 | 0 | 0 | 0 |
| Shrimp-S | 220 c.f.u./ml | 2 | 0 | 0 | 11 | 2 | 0 | 0 |
| Dye-S | 0 | 0 | 0 | 0 | 0 | 0 | 0 | 0 |
| DEYolk | 0 | 0 | 0 | 0 | 0 | 0 | 0 | 0 |
| EYolk | 0 | 0 | 0 | 0 | 0 | 0 | 0 | 0 |
| Chicken | 20 c.f.u./ml | 0 | 0 | 0 | 1 | 0 | 0 | 0 |
| Shrimp | 12 | 2 | 0 | 0 | 12 | 2 | 0 | 0 |
| Dye | 0 | 0 | 0 | 0 | 0 | 0 | 0 | 0 |
| Control | 0 | 0 | 0 | 0 | 0 | 0 | 0 | 0 |

TABLE 9

T-22, 37° C. After overnight selective inhibition

| Media Sample | TSA 10*-2 | TSA 10*-3 | HE 10*-2 | HE 10*-3 |
|---|---|---|---|---|
| DEYolk-S | TNTC | TNTC | TNTC S. Typhimurium | TNTC S. Typhimurium |
| EYolk-S | TNTC | TNTC | TNTC S. Typhimurium | TNTC S. Typhimurium |
| Chicken-S | TNTC | TNTC | TNTC E. coli, Few st. | TNTC E. coli, Few st |
| Shrimp-S | TNTC | TNTC | TNTC E. coli, Few st | TNTC E. coli, Few st. |
| Dye-S | TNTC | TNTC | TNTC S. Typhimurium | TNTC S. Typhimurium |
| DEYolk | TNTC | TNTC | TNTC S. Typhimurium | TNTC S. Typhimurium |
| E. Yolk | 0 | 0 | 0 | 0 |
| Chicken | TNTC | TNTC | TNTC E. coli ? | TNTC E. coli ? |
| Shrimp | TNTC | TNTC | TNTC E. coli, Few st | TNTC E. coli, Few st. |
| Dye | 0 | 0 | 0 | 0 |
| Control | TNTC | TNTC | TNTC S. Typhimurium | TNTC S. Typhimurium |

TABLE 10

Colony Morphology:
5 Hrs/42° C. Lysine Rxn on HE Agar (10 ul/plate)

| Sample | Colony Color | Possible Organism |
|---|---|---|
| Spiked | | |
| DEYolk-S | Blue green | S. typhimurium |
| Eyolk-S | Blue Green | S. typhimurium |
| Chicken-S | Salmon, Bile Precipitation | E. coli |
| Shrimp-S | Salmon, Bile Precipitation | E. coli |
| Dye-S | Blue Green | S. typhimurium |
| Unspiked | | |
| DEYolk | Blue Green | S. typhimurium |
| Eyolk | No Growth | |
| Chicken | Salmon, Bile Precipitation | E. coli |

TABLE 10-continued

Colony Morphology:
5 Hrs/42° C. Lysine Rxn on HE Agar (10 ul/plate)

| Sample | Colony Color | Possible Organism |
|---|---|---|
| Shrimp | Salmon, Bile Precipitation; Blue Green | E. coli S. typhimurium |
| Dye | No Growth | |
| Control | Blue Green | S. typhimurium |

TABLE 11

Lysine Reaction

| Media | S1 | S2 | S3 | S4 | S5 | S6 | S7 | S8 | S9 |
|---|---|---|---|---|---|---|---|---|---|
| 1 Hr | Light Green | Light Green | Yell-Green | Yell-Green | Light Red | Yell-Green | Yell-Green | Yell-Green | Grey Green |
| 2 Hr | Light Green | Light Green | Yell-Green | Yell-Green | Light Red | Yell-Green | Yell-Green | Yell-Green | Purple Grey |
| 3 Hr | Light Green | Light Green | Yell-Green | Yellow | Light Red | Yell-Green | Yell-Green | Yell-Green | Purple |
| 4 Hr | Purple | Purple | Purple | Yellow | Fuchia | Yell-Green | Yell-Green | Yell-Green | Purple |
| 5 Hr | Dark Purple | Dark Purple | Purple | Yellow | Fuchia | Yell-Green | Yell-Green | Purple Grey | Purple |
| 6 Hr | Dark Purple | Dark Purple | Purple | Yellow | Fuchia | Yell-Green | Yell-Green | Grey Purple | Purple |
| Overnight | V. Dark Purple | V. Dark Purple | Light Grey | Yellow | Dark Fuchia | Yell-Green | Yell-Green | Grey | Purple |

| Media | S10 | S11 | Negative |
|---|---|---|---|
| 1 Hr | Light Red | Light Green | Yellow |
| 2 Hr | Light Red | Light Green | Yellow |
| 3 Hr | Light Red | Green Grey | Yellow |
| 4 Hr | Amber | Purple | Yellow |
| 5 Hr | Amber | Dark Purple | Yellow |
| 6 Hr | Amber | Dark Purple | Yellow |
| Overnight | Amber | Very Dark Purple | Yellow |

TABLE 12

$H_2S$ Reaction

| Media | S1 | S2 | S3 | S4 | S5 | S6 | S7 | S8 | S9 |
|---|---|---|---|---|---|---|---|---|---|
| 1 Hr | (−) | (−) | (−) | (−) | (−) | (−) | (−) | (−) | (−) |
| 2 Hr | wk1+ | wk1+ | (−) | wwk1+ | wk1+ | (−) | (−) | (−) | wk1+ |
| 3 Hr | 2+ | 2+ | wk1+ | 2+ | 2+ | (−) | (−) | wk1+ | 2+ |
| 4 Hr | 3+ | 3+ | 2+ | 3+ | 3+ | (−) | (−) | wk1+ | 3+ |
| 5 Hr | 4+ | 4+ | 3+ | 3+ | 4+ | (−) | (−) | wk1+ | 4+ |
| 6 Hr | 4+ | 4+ | 3+ | 4+ | 4+ | (−) | (−) | 1+ | 4+ |
| Overnight | 4+ | 4+ | 4+ | 4+ | 4+ | (−) | (−) | 1+ | 4+ |

| Media | S10 | S11 | Negative |
|---|---|---|---|
| 2 Hr | (−) | 1+ | (−) |
| 3 Hr | (−) | 2+ | (−) |
| 4 Hr | (−) | 3+ | (−) |
| 5 Hr | (−) | 4+ | (−) |
| 6 Hr | (−) | 4+ | (−) |
| Over-night | (−) | 4+ | (−) |

TABLE 13

MUCAP REACTION

| Media | S1 | S2 | S3 | S4 | S5 | S6 | S7 | S8 | S9 |
|---|---|---|---|---|---|---|---|---|---|
| 5' | BGr | BGr | BGr-1+ | BGr | BGr | BGr | BGr | BGr | 1+ |
| 10' | 1+ | 2+ | 2+ | BGr | BGr | BGr | BGr | wk1+ | 2+ |
| 15' | 2+ | 2+ | 3+ | BGr | 1+ | BGr | BGr | 1+ | 2+ |
| 4 Hr | | | | | | | | | |
| 5 Hr | | | | | | | | | |
| 6 Hr | | | | | | | | | |
| Overnight | | | | | | | | | |

TABLE 13-continued

| | MUCAP REACTION | | |
|---|---|---|---|
| Media | S10 | S11 | Negative |
| 5' | BGr | 2+ | BGr |
| 10' | BGr | 3+ | BGr |
| 15' | BGr | 4+ | BGr |
| 4 Hr | | | |
| 5 Hr | | | |
| 6 Hr | | | |
| Over-night | | | |

TABLE 14

Growth History: 1/15/97 > 1/17/97

| Sample | T0-PCA | T4-TSA | T4-HE | T22-TSA | T22-HE | Aft. Rxn 27 Hrs | Lys | H2S | Mcap 10' |
|---|---|---|---|---|---|---|---|---|---|
| DEYolk-S | 0 | 20 cfu/ml | 0 | TNTC | T-St | St | + | + | 1+ |
| EYolk-S | 0 | 0 | 0 | TNTC | T-St | St | + | + | 2+ |
| Chicken-S | 8 | 20 cfu/ml | 0 | TNTC | TNTC Ec, Few St | Ec | + | + | 2+ |
| Shrimp-S | 129 | 220 cfu/ml | 0 | TNTC | TNTC Ec, Few St | Ec | Neg | + | Bgr |
| Dye-S | 0 | 0 | 0 | TNTC | T-St | St | Neg* | + | Bgr |
| DEYolk | — | 0 | 0 | TNTC | T-St | St? | Neg | Neg | Bgr |
| EYolk | — | 0 | 0 | 0 | 0 | 0 | Neg | Neg | Bgr |
| Chicken | — | 20 cfu/ml | 0 | TNTC | T-Ec | Ec | Wk+ | Wk+ | Wk1+ |
| Shrimp | — | 240 cfu/ml | 0 | TNTC | T-Ec, Few St | Ec + St | + | + | 2+ |
| Dye | — | 0 | 0 | 0 | 0 | 0 | Neg* | Neg | Bgr |
| Control | — | 0 | 0 | TNTC | T-St | St | + | + | 3+ |

*Difficult to interprete color change due to red colortion of dye

TABLE 15 of Colonies on both HE Agar and TSA: 50 μl Stomached Samples, 37° C.

| Sample | HE 10*-2 | TSA 10*-2 | HE 10*-3 | TSA 10*-3 |
|---|---|---|---|---|
| Chicken | 0 | 0 | 0 | 0 |
| Shrimp | 2 BG | 48 | 0 | 5 |
| Dry Milk | 0 | 0 | 0 | 0 |
| Whole Black Pepper | 0 | 62 | 0 | 25 |
| Ground Pork Sausage | 30 g 13 BG | 123 | 2 or | 53 |
| Ground beef | 0 | 0 | 0 | 0 |
| Milk Chocolate | 0 | 5 | 0 | 0 |

TABLE 16 of colonies on HE; TSA at T-4

| Media Sample | TSA 10*-2 | TSA 10*-3 | HE 10*-2 | HE 10*-3 |
|---|---|---|---|---|
| Chicken-spiked | 9 | 6 | 2 | 0 |
| Shrimp-spiked | 64 | 12 | 23 BG | 2 BG |
| Dry Milk-spiked | 0 | 0 | 0 | 0 |
| Whole Pepper-spiked | TNTC | 27 | 0 | 0 |
| Ground Pork Sausage-spiked | 139 | 37 | 65 or 20 BG | 5 or 5 BG |
| Ground Beef-spiked | 6 | 0 | 40 or | 0 |
| Milk Chocolate-spiked | 3 | 0 | 0 | 0 |
| Chicken-unspiked | 5 | 0 | 1 or 3 BG | 0 |
| Shrimp-unspiked | 130 | 21 | 18 BG | 2 BG |
| Dry Milk-unspiked | 1 | 0 | 0 | 0 |
| Whole Pepper-unspiked | TNTC | 24 | 0 | 0 |
| Ground Pork Sausage-unspiked | 129 | 50 | 60 or 22 BG | 4 or |
| Ground Beef-unspiked | 10 | 0 | 2 or 3 BG | 0 |
| Milk Chocolate-unspiked | 5 | 1 | 0 | 0 |
| Control | 0 | 0 | 0 | 0 | or = Orange
BG = Blue Green

TABLE 17

Lysine Decarboxylation Test Results

| Media | S1 | S2 | S3 | S4 | S5 | S6 | S7 | S8 | S9 |
|---|---|---|---|---|---|---|---|---|---|
| 1 Hr | Yellow | Yellow | Yellow | Yellow | Yellow | Yellow | Yellow | Yellow | Yellow |
| 2 Hr | Yellow | Yellow | Yellow | Grey | Grey | Grey | Grey | Yellow | Yellow |
| 3 Hr | Yellow | Yellow | Yellow | Purple Grey | Purple Grey | Light Purple | Purple Grey | Yellow | Grey |
| 4 Hr | Light Grey | Light Grey | Yellow | Light Purple | Dark Purple | Purple | Purple | Grey | Dark Grey |
| 5 Hr | Grey | Grey | Yellow | Dark Purple | Dark Purple | Purple Grey | Dark Purple | Purple Grey | Grey |
| 6 Hr | Purple Grey | Grey | Yellow | Dark Purple | Dark Purple | Purple Grey | Dark Purple | Purple | Grey |
| Overnight | Light Grey | Yellow Grey | Yellow | Dark Purple | Light Grey-Yellow | Light Grey | Dark Purple | Yellow Grey | Yellow Grey |

| Media | S10 | S11 | S12 | S13 | S14 | S15 | Negative |
|---|---|---|---|---|---|---|---|
| 1 Hr | Yellow | Yellow | Yellow | Yellow | Yellow | Yellow Green | Yellow |
| 2 Hr | Yellow | Yellow | Grey | Yellow | Yellow | Grey | Yellow |
| 3 Hr | Yellow | Yellow | Light Purple | Purple Grey | Yellow | Purple Grey | Yellow |
| 4 Hr | Yellow | Yellow | Dark Purple | Purple | Yellow | Purple | Yellow |
| 5 Hr | Yellow | Yellow | Dark Purple | Purple Grey | Yellow | Dark Purple | Yellow |
| 6 Hr | Yellow | Yellow | Dark Purple | Purple Grey | Yellow | Dark Purple | Yellow |
| Overnight | Yellow | Yellow | Yellow Grey | Light Purple Grey | yellow | Dark Purple | Yellow |

TABLE 18

H$_2$S Test Results

| Media | S1 | S2 | S3 | S4 | S5 | S6 | S7 | S8 | S9 |
|---|---|---|---|---|---|---|---|---|---|
| 1 Hr | Neg. | Neg. | Neg. | Neg | Neg. | Neg. | Neg. | Neg. | Neg. |
| 2 Hr | Neg. | Neg. | wk+ | wk+ | neg. | wk+ | 1+ | wk+ | wk+ |
| 3 Hr | Neg. | Neg. | 1+ | 1+ | wk+ | wk2+ | wk2+ | wk+ | wk1+ |
| 4 Hr | wk+ | wk1+ | 1+ | 2+ | 2+ | 2+ | 3+ | 1+ | 2+ |
| 5 Hr | wk+ | 1+ | wk2+ | 3+ | 3+ | 3+ | 4+ | 1+ | 3+ |
| 6 Hr | wk+ | 2–3+ | 2+ | 4+ | 4+ | 4+ | 4+ | 2+ | 4+ |
| Overnight | 1+ | 3+ | 4+ | 4+ | 4+ | 4+ | 4+ | 3+ | 4+ |

| Media | S10 | S11 | S12 | S13 | S14 | S15 | Negative | S15-Retest |
|---|---|---|---|---|---|---|---|---|
| 1 Hr | Neg. | Neg. | Neg. | Neg. | Neg. | Neg. | Neg. | Neg. |
| 2 Hr | + | Neg. | Neg. | wk+ | Neg. | Neg. | Neg. | wk1+ |
| 3 Hr | 1+ | Neg. | wk+ | 2+ | Neg. | Neg. | Neg. | 1+ |
| 4 Hr | 1+ | Neg. | 1+ | 3+ | Neg. | Neg. | Neg. | 2+ |
| 5 Hr | 1+ | Neg. | 2+ | 4+ | Neg. | Neg. | Neg. | not read |
| 6 Hr | 2+ | Neg. | 4 + | 4+ | Neg. | Neg. | Neg. | not read |
| Overnight | 2+ | Neg. | 4+ | 4+ | Neg. | Neg. | Neg. | 4+ |

TABLE 19

Growth History: 1/22/97 > 1/23/97

| Sample | T0-TSA From $10^{-2}$ | T0 HE BG Col. From $10^{-2}$ | T0-PCA From $10^{-2}$ | T4-HE BG Col. | T22-HE | TSI: T22Hrs | Aft. Rxn 29–30 Hrs:HE | TSI:T29–30 Hrs | Lys Rxn | H2S Rxn | Mucap Rxn[1] | Result |
|---|---|---|---|---|---|---|---|---|---|---|---|---|
| Chicken-S | 0 | 0 | 4.2 × 10*3 No Flr. | 1 × 10*2 | TNTC Or + BG | A + G: Ec | TNTC Or + BG | A + G: Ec | Wk+ | Wk+ | Pos | +St |
| Shrimp-S | 4.8 × 10*3 | 2 × 10*2 | TNTC, No Flr. | 2.3 × 10*3 | TNTC Or + BG | H2S + G: St | TNTC Or | A + G: Ec | Wk+ | Wk+ | Pos | +St |
| Dry Milk-S | 0 | 0 | 3, No Flr. | 0 | TNTC | A + G: | TNTC | H2S + G: Neg | Pos | Pos | +St |

TABLE 19-continued

Growth History: 1/22/97 > 1/23/97

| Sample | T0-TSA From $10^{-2}$ | T0 HE BG Col. From $10^{-2}$ | T0-PCA From $10^{-2}$ | T4-HE BG Col. | T22-HE | TSI: T22Hr s | Aft. Rxn 29–30 Hrs:HE | TSI:T29–30 Hrs | Lys Rxn | H2S Rxn | Mucap Rxn[1] | Result |
|---|---|---|---|---|---|---|---|---|---|---|---|---|
| WhlBlkPprs-S | 6.2 × 10*3 | 0 | 3 × $10^2$ TNTC, Flr. | 0 | Or + BG TNTC BG | Ec H2S + G: St | Or + BG TNTC BG | St H2S + G St | Pos | Pos | Pos | +St |
| GrPrkSau-S | 1.2 × 10*4 | 1.3 × 10*3 | TNTC, Flr. | 2 × 10*3 | TNTC Or + BG | A + G: Ec | TNTC Or + BG | H2S + G: St | Pos | Pos | Pos | +St |
| GrBeef-S | 0 | 0 | 5.5 × 10*3 Wk Flr. | 0 | TNTC Or + BG | H2S + G: St | TNTC Or + BG | H2S + G: St | Pos | Pos | Pos | +St |
| MilkChoc-S | 0 | 0 | 4.8 × 10*3 Flr. | 0 | TNTC Or ° BG | H2S + G: St | TNTC BG | H2S + G: St | Pos | Pos | Pos | +St |
| Chicken | NA | NA | NA | 3 × 10*2 | TNTC Or + BG | H2S + G: St | TNTC OR + BG | A + G: Ec | Pos | Pos | Pos | +St |
| Shrimp | NA | NA | NA | 1.8 × 10*3 | TNTC Or + BG | H2S + G: St | TNTC Or + BG | A + G: Ec | Wk+ | Pos | Pos | +St |
| DryMilk | NA | NA | NA | 0 | TNTC Or | A + G: Ec | TNTC Or | A + G: Ec | Neg | Wk+ | Bgr | Neg |
| WhlBlkPprs | NA | NA | NA | 0 | 0 | 0 | 0 | 0 | Neg | Neg | Bgr | Neg |
| GrPrkSau | NA | NA | NA | 2.2 × 10*3 | TNTC Or + BG | H2S + G: St | TNTC Or + BG | A + G: Ec | Pos | Pos | Pos | +St |
| GrBeef | NA | NA | NA | 3 × 10*2 | TNTC Or + BG | H2S + G: St | TNTC Or + BG | H2S + G: St | Pos | Pos | Pos | +St |
| Milk Choc | NA | NA | NA | 0 | 0 | 0 | 0 | 0 | Neg | Neg | Bgr | Neg |
| Control-S | NA | NA | NA | 0 | TNTC BG | H2S + G: St | TNTC BG | H2S + G: St | Pos | Pos | Pos | +St |

Flr. = Fluorescence;
BG = Blue Green Colonies;
Or = Orange Colonies;
TNTC = Too Numerous to Count
H2S = H2S production & blackening;
G = Gas production,
A = Acid slant(yellow),
Bgr = Background fluorescence

TABLE 20

MUCAP Test Results

| Media | S1 | S2 | S3 | S4 | S5 | S6 | S7 | S8 | S9 |
|---|---|---|---|---|---|---|---|---|---|
|  | 4+ | 3+ | 2+ | 4+ | 4+ | 4+ | 4+ | 4+ | 3+ |

| Media | S10 | S11 | S12 | S13 | S14 | S15 | Neg. |
|---|---|---|---|---|---|---|---|
|  | BGr | BGr | 4+ | 4+ | BGr | 4+ | Neg BGr |

TABLE 21 # of colonies on HE and TST @ $T_{22}$

| Media Sample | TSA 10*-2 | TSA 10*-3 | HE 10*-2 | HE 10*-3 | TSI 10*-2 | TSI 10*-3 |
|---|---|---|---|---|---|---|
| Chicken-spiked | TNTC | Or + BG | TNTC | TNTC | A + G | EC? |
| Shrimp-spiked | TNTC | Or + BG | TNTC | TNTC | $H_2S$ + G | St? |
| Dry Milk-spiked | TNTC | Or + BG | TNTC | TNTC | A + G | EC? |
| Whole Pepper-spiked | TNTC | + BG | TNTC | TNTC | $H_2S$ + G | St? |
| Ground Pork Sausage-spiked | TNTC | Or + BG | TNTC | TNTC | A + G | EC? |
| Ground Beef-spiked | TNTC | Or + BG | TNTC | TNTC | $H_2S$ + G | St? |
| Milk Chocolate-Spiked | TNTC | Or + BG | TNTC | TNTC | $H_2S$ + G | St? |
| Chicken-unspiked | TNTC | Or + BG | TNTC | TNTC | $H_2S$ + G | St? |
| Shrimp-unspiked | TNTC | Or + BG | TNTC | TNTC | $H_2S$ + G | St? |
| Dry Milk-unspiked | TNTC | Or | TNTC | TNTC | A + G | EC? |
| Whole Pepper-unspiked | 0 | 0 | 0 | 0 | 0 | 0 |
| Ground Pork Sausage-unspiked | TNTC | Or + BG | TNTC | TNTC | $H_2S$ + G | St? |
| Ground Beef-unspiked | TNTC | Or + BG | TNTC | TNTC | $H_2S$ + G | St? |
| Milk Chocolate-unspiked | 0 | 0 | 0 | 0 | 0 | 0 |
| Control-S | TNTC | BG | TNTC | TNTC | $H_2S$ + G | St? |

A = acid slant
G = gas
$H_2S$ = $H_2S$ prod. blackening
EC = *E. coli*
St-*S. typhimurium*

TABLE 22

Colony Morphology:
After 5 hrs/42° C. Biochemical Rxn on HE Agar (10 μl/plate)

| Sample | HE Morphology | TSI Result | Possible Organism |
|---|---|---|---|
| Chicken-spiked | Orange-TNTC/BP BG-Few | A + G | E. coli (Hard to pick colonies) |
| Shrimp-spiked | Orange-TNTC/BP | A + G | E. coli (Hard to pick colonies) |
| Dry Milk-spiked | Orange-TNTC BP BG-Few | $H_2S$ + G | St |
| Whole Black Pepper-spiked | BG-TNTC | $H_2S$ + G | St |
| Ground Pork Sausage-spiked | Orange-TNTC/BP BG-Few | $H_2S$ + G | St |
| Ground Beef-spiked | Orange-TNTC/BP BG-Few | $H_2S$ + G | St |
| Milk Chocolate-spiked | BG-TNTC | $H_2S$ + G | St |
| Control-S | BG-TNTC | $H_2S$ + G | St |
| Chicken-unspiked | Orange-TNTC/BP BG-Few | A + G | E. Coli (Hard to pick colonies) |
| Shrimp-unspiked | Orange-TNTC/BP BG-Few | A + G | E. coli (Hard to pick colonies) |
| Dry Milk-unspiked | Orange-TNTC/BP | A + G | E. coli (Hard to pick colonies) |
| Whole Black Pepper-unspiked | 0 | — | — |
| Ground Pork Sausage-unspiked | Orange-TNTC/BP BG-Few | A + G | E. coli (Hard to pick colonies) |
| Ground Beef-unspiked | Orange-TNTC/BP BG-Few | $H_2S$ + G | St |
| Milk Chocoiate-unspiked | 0 | — | — |
| Control | — | — | — |

BP = bile precipitation
A = acid slant
G = gas production
$H_2S$ = $H_2S$ production black color

What is claimed is:

1. A rapid screening method for the detection and identification of target microorganisms in a sample which may contain both target microorganisms and competing non-target microorganisms, said method comprising the steps of:
   pre-enriching a sample in a growth medium;
   adding at least one inhibitor of the non-target microorganisms to the growth medium to discourage the growth of non-target microorganisms and to encourage the growth of the target microorganisms;
   incubating the sample in the growth medium including the at least one inhibitor for a predetermined amount of time;
   performing biochemical assays specific for identification of the target microorganisms; and
   detecting the presence of the target microorganisms in the sample.

2. The method as set forth in claim 1, wherein the growth medium is mildly inhibitory.

3. The method as set forth in claim 1 further including the step of screening out samples found to be negative for the target microorganism.

4. The method as set forth in claim 1, wherein the sample is further defined as including a mixed culture of microorganisms.

5. The method as set forth in claim 1, wherein said pre-enriching step is approximately two to six hours in duration.

6. The method as set forth in claim 5, wherein said pre-enriching step is approximately four hours in duration.

7. The method as set forth in claim 1, wherein the sample is incubated with a growth medium and the at least one inhibitor of non-target microorganisms for between approximately six hours to eight hours.

8. The method as set forth in claim 7, wherein the sample is incubated with the growth medium and the at least one inhibitor of non-target microorganisms for approximately eight hours.

9. The method as set forth in claim 1, wherein the sample is incubated with the growth medium containing biochemical reagents specific for identification of the target microorganism for approximately twelve to fourteen hours.

10. The method as set forth in claim 9, wherein the sample is incubated with the growth medium containing biochemical reagents specific for identification of the target microorganism for approximately twelve hours.

11. The method as set forth in claim 1, wherein the sample is incubated at a temperature ranging from approximately 33° C. to 43° C.

12. The method as set forth in claim 1, wherein the sample is incubated at approximately 35° C.

13. The method as set forth in claim 1, wherein the growth medium includes modified-TSB and an antibiotic.

14. The method as set forth in claim 13, wherein the antibiotic includes novobiocin.

15. The method as set forth in claim 1, wherein the inhibitor includes a mixture of magnesium chloride, malachite green, and crystal violet.

16. The method as set forth in claim 1, wherein the inhibitor includes selenite-cysteine tetrathionate.

17. A method as set forth in claim 1, wherein the biochemical assays include an $H_2S$ test strip.

18. A method as set forth in claim 1, wherein the biochemical assays include a lysine decarboxylase detection reagent.

19. A method as set forth in claim 1, wherein the biochemical assays include arginine decarboxylase and ornithine decarboxylase.

20. A method as set forth in claim 1, wherein the biochemical assays include substrate utilization reactions including as a substrate dulcitol, propylene glycol, and glucuronate.

21. A method as set forth in claim 1, wherein the biochemical assays include methylumbelliferyl caprylate (MUCAP) and. methylumbelliferyl glucuronide (MUG).

22. A method as set forth in claim 21, wherein the methylumbelliferyl caprylate (MUCAP) and methylumbelliferyl glucuronide (MUG) are in solution.

23. A method as set forth in claim 21, wherein the methylumbelliferyl caprylate (MUCAP) and methylumbelliferyl glucuronide (MUG) are in solid form.

24. The method as set forth in claim 1 further including the step of performing an immunological assay on the sample contained in the predetermined amount of growth medium.

25. The method as set forth in claim 1, further including the step of at least partially homogenizing the sample in the growth medium.

26. The method as set forth in claim 1 further including the step of transferring a predetermined amount of the growth media containing the sample into at least one media receiving vessel containing biochemical reagents specific for the identification of the target microorganisms.

27. The method as set forth in claim 26, wherein said transferring step is substantially automated.

28. The method as set forth in claim 26, wherein said transferring step is substantially manual.

29. A system for rapid screening for the detection and identification of target microorganisms in a sample which may contain both target microorganisms and competing non-target microorganisms, said system comprising:

container means for containing a sample and a growth medium;

growth inhibition means for inhibiting the growth of non-target microorganisms in the growth medium to discourage the growth of non-target microorganisms and to encourage the growth of the target microorganisms;

biochemical reagent means for identification of the target microorganisms in the sample; and detection means for detecting the presence of the target microorganisms in the sample.

30. The system as set forth in claim 29, wherein said growth medium includes modified-TSB and an antibiotic.

31. The system as set forth in claim 30, wherein said antibiotic includes novobiocin.

32. The system as set forth in claim 29, wherein said growth inhibition means include a mixture of magnesium chloride, malachite green, and crystal violet.

33. The system as set forth in claim 29, wherein the inhibitor includes selenite-cysteine tetrathionate.

34. The system as set forth in claim 29, wherein said biochemical reagent means include an $H_2S$ test strip.

35. The system as set forth in claim 29, wherein said biochemical reagent means include a lysine decarboxylase detection reagent.

36. The system as set forth in claim 29, wherein the biochemical reagents include arginine decarboxylase and ornithine decarboxylase.

37. The method as set forth in claim 29, wherein the biochemical reagents include substrate utilization reactions including as a substrate dulcitol, propylene glycol, and glucuronate.

38. The system as set forth in claim 29, wherein said biochemical reagent means include methylumbelliferyl caprylate (MUCAP) and methylumbelliferyl glucuronide (MUG).

39. The system as set forth in claim 38, wherein the methylumbelliferyl caprylate (MUCAP) and methylumbelliferyl glucuronide (MUG) are in solution.

40. The system as set forth in claim 38, wherein the methylumbelliferyl caprylate (MUCAP) and methylumbelliferyl glucuronide (MUG) are in solid form.

41. The system as set forth in claim 29, wherein said detection means includes immunological assay means for performing immunological assays on said sample.

42. The system as set forth in claim 29, wherein said container means for containing said sample and growth medium includes a resilient plastic bag.

43. A methylumbelliferyl caprylate (MUCAP) reagent for use in diagnostic microbiological analysis, said reagent comprising a solution of methylumbelliferyl caprylate dissolved in ethyl acetate.

44. The reagent as set forth in claim 43, wherein the concentration of methylumbelliferyl caprylate in said solution ranges from approximately 0.05% to 10%.

45. The reagent as set forth in claim 44, wherein the concentration of methylumbelliferyl caprylate in said solution is approximately 0.1%.

* * * * *